(12) United States Patent
Djamgoz

(10) Patent No.: US 11,634,398 B2
(45) Date of Patent: Apr. 25, 2023

(54) TREATMENT OF CANCER/INHIBITION OF METASTASIS

(71) Applicant: Celex Oncology Ltd., London (GB)

(72) Inventor: Mustafa Djamgoz, London (GB)

(73) Assignee: Celex Oncology Limited, London (GB)

( * ) Notice: Subject to any disclaimer, the term of this patent is extended or adjusted under 35 U.S.C. 154(b) by 25 days.

(21) Appl. No.: 16/576,178

(22) Filed: Sep. 19, 2019

(65) Prior Publication Data

US 2020/0017457 A1 Jan. 16, 2020

Related U.S. Application Data

(63) Continuation of application No. 16/002,555, filed on Jun. 7, 2018, now abandoned, which is a continuation of application No. 14/881,952, filed on Oct. 13, 2015, now abandoned, which is a continuation of application No. 13/879,146, filed as application No. PCT/GB2010/001908 on Oct. 13, 2010, now abandoned.

(51) Int. Cl.

| | |
|---|---|
| *C07D 295/15* | (2006.01) |
| *A61K 31/00* | (2006.01) |
| *A61K 31/428* | (2006.01) |
| *A61K 31/495* | (2006.01) |
| *A61K 31/138* | (2006.01) |
| *A61K 31/167* | (2006.01) |
| *A61K 31/19* | (2006.01) |
| *A61K 31/4458* | (2006.01) |
| *C07D 241/04* | (2006.01) |
| *C07D 277/82* | (2006.01) |

(52) U.S. Cl.
CPC ............ *C07D 295/15* (2013.01); *A61K 31/00* (2013.01); *A61K 31/138* (2013.01); *A61K 31/167* (2013.01); *A61K 31/19* (2013.01); *A61K 31/428* (2013.01); *A61K 31/4458* (2013.01); *A61K 31/495* (2013.01); *C07D 241/04* (2013.01); *C07D 277/82* (2013.01)

(58) Field of Classification Search
CPC ..................................................... A61K 31/00
See application file for complete search history.

(56) References Cited

U.S. PATENT DOCUMENTS

| | | |
|---|---|---|
| 2004/0167079 A1 | 8/2004 | Tidmarsh |
| 2009/0247535 A1 | 10/2009 | Pitt |
| 2010/0221246 A1* | 9/2010 | Goydos ................. A61K 31/27 424/133.1 |
| 2013/0203764 A1 | 8/2013 | Djamgoz |

FOREIGN PATENT DOCUMENTS

| | | | | |
|---|---|---|---|---|
| JP | 2013539778 A | 10/2013 | | |
| WO | WO-03088915 A1 | 10/2003 | | |
| WO | WO-03088915 A2 * | 10/2003 | .......... | C07D 233/76 |
| WO | WO-2009105230 A2 * | 8/2009 | ............. | C07K 16/32 |
| WO | WO-2009105230 A2 | 8/2009 | | |
| WO | WO-2010033581 A * | 3/2010 | .......... | A61K 31/553 |
| WO | WO-2010033581 A1 | 3/2010 | | |
| WO | WO-2012049440 A1 | 4/2012 | | |

OTHER PUBLICATIONS

Jerling, Clinical Pharmacokinets of Ranolazine, Clin Pharmacokinetc. 2006; 45(5): 469-491.*
Djamgoz, Oncofoetal ion channels may present new targets for anti-cancer agents, Pharmacy in practice, Medicom, Kingston upon Thames, vol. 17, No. 2, pp. 60-62, 2007.*
Abdul et al., Voltage-gated Sodium Ion Channels in Prostate Cancer: Expression and Activity, Anticancer Research 22:1727-1730 (2002).*
Wang et al., State- and Use-Dependent Block of Muscle Nav1.4 and Neuronal Nav1.7 Voltage-Gated Na Channel Isoforms by Ranolazine, Mol. Pharm., vol. 73(3), Sep. 2007, pp. 940-948.*
Grimes et al., FEBS Letters, 369 (1995) 290-294.*
Speyer et al., Proceedings of the annual meeting of the American association for cancer research, 101st annual meeting, Washington, DC, Apr. 17-21, 2010, vol. 51, Apr. 2010.*
Samudio et al., Pharmacologic inhibition of fatty acid oxidation sensitizes human leukemia cells to apoptosis induction, J. of Clin. Inv., vol. 120, No. 1. Jan. 2010, pp. 142-156.*
Akamatsu et al., Riluzole Induces Apoptotic Cell Death in Human Prostate Cancer Cells via Endoplasnnc Reticulmn Stress, Anticancer Research 29:2195-2204 (2009).*
Fraser et al., Voltage-Gated Sodium Channel Expression and Potentiation of Human Breast Cancer Metastasis, Clin Cancer Res 2005; 11 (15) Aug. 1, 2005, pp. 5381-5389.*
Onkal et al., Molecular pharmacology of voltage-gated sodium channel expression in metastatic disease: clinical potential of neonatal Nav1.5 in breast cancer, Eur J Pharmacol, Dec. 25, 2009;625(1-3):206-19, Epub Oct. 14, 2009.*
Abdul, M., et al., "Voltage-Gated Sodium Ion Channels in Prostate Cancer: Expression and Activity", Anticancer Research, 22(3), (2002), 1727-1730.
Akamatsu, K., et al., "Riluzole Induces Apoptotic Cell Death in Human Prostate Cancer Cells via Endoplasmic Reticulum Stress", Anticancer Research, 29(6), (2009), 2195-2204.
Antzelevitch, C., et al., "Electrophysiological Effects of Ranolazmine, a Novel Antianginal Agent With Antiarrhythmic Properties," Circulation, American Heart Association/Resuscitation Science Symposium; New Orleans,LA, USA; 110(8), 2004, 904-910.
"U.S. Appl. No. 13/879,146, Non Final Office Action dated Apr. 13, 2015", 19 pgs.

(Continued)

*Primary Examiner* — Svetlana M Ivanova
(74) *Attorney, Agent, or Firm* — Womble Bond Dickinson (US) LLP

(57) ABSTRACT

Substances and methods are dislosed for reducing or preventing metastatic behaviour in VGSC expressing cancer by the effect of at least reducing the persistent part of the voltage gated sodium channel current without eliminating the transient part. Inhibition of metastatic cell behaviours such as detachability, lateral motility, transverse migration and invasiveness is demonstrated using the known drugs ranolazine and riluzole.

7 Claims, 27 Drawing Sheets

(56) References Cited

OTHER PUBLICATIONS

"U.S. Appl. No. 13/879,146, Response filed Feb. 6, 2015 Restriction Requirement filed Aug. 6, 2014", 9 pgs.

"U.S. Appl. No. 13/879,146, Restriction Requirement dated Aug. 6, 2014", 14 pgs.

"Chinese Application No. 201080070348.8, Office Action dated Jun. 27, 2017", w/ English Translation, (dated Jun. 27, 2017), 12 pgs.

Diss, J. K. J., et al., "[beta]-subunits of voltage-gated sodium channels in human prostate cancer: quantitative in vitro and in vivo analyses of mRNA expression", Prostate cancer and prostatic diseases 11.4, (2008), 325-333.

Djamgoz, M., "Oncofoetal ion channels may present new targets for anti-cancer agents", Pharmacy in Practice, 17(2), (Mar. 1, 2007), 60-62, and 64.

"European Application Serial No. 16020321.2, Extended European Search Report dated Jan. 18, 2017", (dated Jan. 18, 2017), 19 pgs.

Fraser, S. P., et al., "Voltage-Gated Sodium Channel Expression and Potentiation of Human Breast Cancer Metastasis", Clin. Cancer Res., 11(15), (2005), 5381-5389.

Grimes, J. A., et al., "Differential expression of voltage-activated Na+ currents in two prostatic tumor cell lines: contribution to invasiveness in vitro", FEBS Letters, 369, (1995), 290-294.

"International Application Serial No. PCT/GB2010/001908, International Search Report dated Jun. 30, 2011", 5 pgs.

Isbilen, Banu, et al., "Docosahexaenoic acid (omega-3) blocks voltage-gated sodium channel activity and migration of MDA-MB-231 human breast cancer cells", The international journal of biochemistry & cell biology 38.12, (2006), 2173-2182.

"Japanese Application No. 2016-019871, Office Action dated Jul. 31, 2017", w/ English Translation, (dated Jul. 31, 2017), 11 pgs.

Jerling, Markus, "Clinical Pharmacokinetics of Ranolazine," *Clin Pharmacokinetic*, 2006, vol. 45(5), pp. 469-491.

Onkal, Rustem, et al., "Molecular pharmacology of voltage-gated sodium channel expression in metastatic disease: clinical potential of neonatal Nav1. 5 in breast cancer", European journal of pharmacology 625.1-3, (2009), 206-219.

Palmer, C. P., et al., "Single cell adhesion measuring apparatus (SCAMA): application to cancer cell lines of different metastatic potential and voltage-gated NA+ channel expression", Eur. Biophys. J., 37, (2008), 359-368.

Roger, Sébastien, et al., "Voltage-gated sodium channels: new targets in cancer therapy?", Current pharmaceutical design 12.28, (2006), 3681-3695.

Samudio, I., et al., "Pharmacologic inhibition of fatty acid oxidation sensitizes human leukemia cells to apoptosis induction", Journal of Clinical Investigation, 120(1), (2010), 142-156.

Speyer, C. L., et al., "The role of metabotropic glutamate receptor-1 in breast cancer tumor progression", (Abstract 1578) In: Proceedings of the 101st Annual Meeting of the American Association for Cancer Research, vol. 70(Issue 8, Suppl. 1), (2010).

Suckow, M., et al., "The anti-ischemia agent ranolazine promotes the development of intestinal tumors in APC(Min/+) mice", Cancer Letters, 209(2), (2004), 165-169.

Vacher, B., et al., "F 15845 inhibits persistent sodium current in the heart and prevents angina in animal models", British journal of pharmacology 156.2, (2009), 214-225.

Wallace, C. H. R., et al., "Inhibition of cardiac voltage-gated sodium channels by grape polyphenols", British journal of pharmacology 149.6, (2006), 657-665.

Wang, et al., "State-and Use-Dependent Block of Muscle Nav1.4 and Neuronal Nav1.7 Voltage-Gated Na Channel Isoformsby Ranolazine", Mol. Pharm., vol. 73(3), (Sep. 2007), 940-948.

Wang, Ya-Jean, et al., "Riluzole-induced block of voltage-gated Na+ current and activation of BK Ca channels in cultured differentiated human skeletal muscle cells", Life sciences 82.1, (2008), 11-20.

Weiss, Steven, et al., "Riluzole protects against cardiac ischaemia and reperfusion damage via block of the persistent sodium current", British journal of pharmacology 160.5, (2010), 1072-1082.

Belardinelli, et al., "Inhibition of the late sodium current as a potential cardioprotective principle: effects of the late sodium current inhibitor ranolazine," *Heart*, 2006, vol. 92(Suppl IV), pp. iv6-iv14.

\* cited by examiner

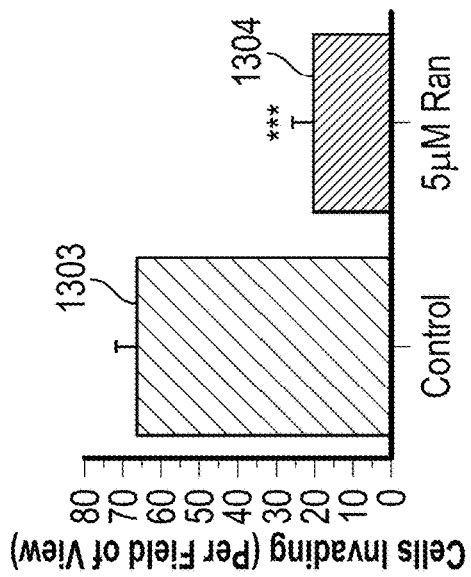
FIG. 13A
FIG. 13B
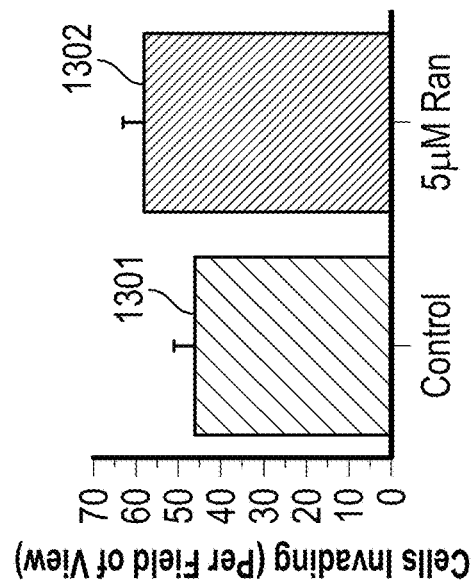
FIG. 13C
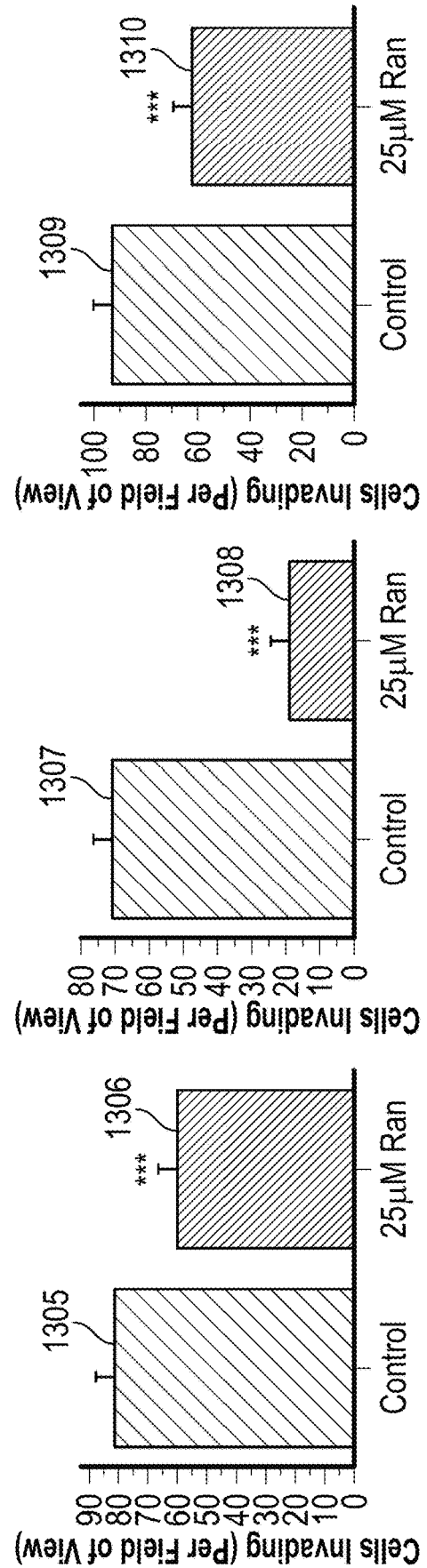
FIG. 13D
FIG. 13E

TREATMENT OF CANCER/INHIBITION OF METASTASIS

CROSS-REFERENCE TO RELATED APPLICATIONS

This application is a continuation of U.S. application Ser. No. 16/002,555, filed Jun. 7, 2018, which is a continuation of U.S. application Ser. No. 14/881,952, filed Oct. 13,2015, which is a continuation of U.S. application Ser. No. 13/791,146, filed Apr. 12, 2013, which is a national stage filing under 35 U.S.C. 371 of International Application PCT/GB2010/001908, filed Oct. 13, 2010, all of which is incorporated by reference herein in its entirety.

BACKGROUND

This invention relates to the treatment of cancer, and is particularly, but not exclusively, concerned with the treatment of metastatic cancer, such as breast or prostate cancer.

Progression of metastatic cancer, such as breast and prostate cancer, is generally considered as comprising five phases, as follows:
1. Genesis, namely the initial transformation of a normal cell into a cancer cell.
2. Proliferation, namely increase in the number of cancer cells to form a primary tumour of increasing size.
3. Switching, during the genesis or proliferation phase, from a condition in which the cancer cells have no potential for metastatic behaviour to a condition in which they do.
4. Detachment of cancer cells from the primary tumour followed by movement of those detached cells into surrounding regions of tissue within the same organ towards the circulation system.
5. Metastasis, namely the movement of the detached cells through the circulation (blood or lymph) to other organs to create secondary tumours in those other organs.

A significant change which takes place in the cell and causes the switch in condition at phase 3 above is the expression of functional voltage-gated sodium channels (VGSCs). In breast cancer it is the Nav1.5 channel which is expressed and in the case of prostate cancer it is the Nav1.7 channel. VGSCs may be expressed in neonatal and/or adult form. In the case of breast cancer, it is the neonatal form of the Nav 1.5 channel (nNav1.5) which is expressed. In the case of prostate cancer, it is not currently known which form is expressed. In the absence of such channels, the cells do not have the potential for invasion and hence metastatic behaviour.

In some cases, the genesis phase involves the growth of cancer cells which, from the outset, have metastatic potential.

Prior Proposals for Preventing Metastasis

Prior to the present invention, the focus in the field has been to try to find a treatment for preventing metastasis by one or more of the following:
(a) preventing the expression of functional VGSCs;
(b) completely blocking the activity of functional VGSCs which have been expressed; or
(c) killing the cells.

The present invention proposes a different approach.

SUMMARY OF THE INVENTION

Current flows intermittently through VGSCs, that is to say the current flows in pulses. It is known that each pulse comprises a transient (or peak) part which is followed by a low-level DC part, known as the late or persistent current. It is also known that appropriate doses of the known drugs ranolazine or riluzole inhibit the persistent part of the current leaving the transient part either unaffected or only reduced partially.

Experimental work, more fully described below, carried out in connection with this invention has demonstrated that:
(i) inhibiting the persistent part of the Nav1.5 and Nav1.7 currents respectively in breast and prostate cancer inhibits metastatic behaviour;
(ii) it is not necessary to inhibit the transient part of these currents in order to inhibit metastatic behaviour;
(iii) appropriate doses of ranolazine or riluzole will inhibit metastatic behaviour without preventing proliferation or destroying the cells of the tumour; and
(iv) the inhibiting effects of ranolazine and riluzole on the persistent part of the current are greater in cells with prior exposure to hypoxia, which is a condition that occurs in growing tumours and makes a critical positive contribution to the metastatic process.

Ranolazine and riluzole are both known for the treatment of cardiac conditions. It is further known that each of them differentially affects the magnitude of the transient and persistent parts of the VGSC currents, the effect being in a dose-dependent manner. High doses of these drugs completely block the VGSC currents. Doses of these, or any other drug, which would have the effect of completely blocking VGSC currents in cardiac tissue would be fatal to the patient because the heart requires these currents in order to carry out its function.

However, in accordance with an aspect of the invention, metastatic behaviour is inhibited or reduced in cancer by administering ranolazine or riluzole, or another substance, at an appropriate dosage to inhibit or reduce the persistent part of the VGSC current without blocking, or at least without completely blocking, the transient part. Thus, metastasis in cancer may be inhibited or reduced in this way without having to administer doses of drugs which would be fatal.

Riluzole has already been proposed in the treatment of certain cancers, in particular prostate cancer and melanoma. In both cases, it was proposed that riluzole should be administered in such a way that the cancerous cells are killed.

In accordance with a further aspect of the invention, which will be more fully explained below, riluzole, or ranolazine, is administered at a dosage level which will inhibit the persistent part of the VGSC current without blocking or completely blocking the transient part and without directly causing cell death.

The fact that metastatic behaviour may be inhibited or reduced without causing cell death may be a significant advantage since recent work has suggested that treating cancer by killing the cells may, at least in some cases, be counter-productive in the sense that whilst there will be a short term benefit, the cancer will nevertheless return and proliferate. Thus, the invention provides the possibility of inhibiting or preventing metastatic behaviour without the potential problems which may arise from actually killing the cancer cells.

Metastatic behaviour involves several stages, namely:
(a) detachment of cells from the tumour;
(b) movement of the detached cells into the surrounding tissue;
(c) movement through that surrounding tissue towards the circulation system; and (d) movement into the circulation system (from which the cells may exit ultimately to form secondary tumours).

Inhibiting or reducing the activity of the cells in any one or more of these stages will therefore contribute to at least a reduction in metastasis. The effect of drugs on each of these sub-stages can be determined, as more fully explained below, by a number of experiments, namely:
(a) testing the effect of the drug on the adhesiveness of the cells;
(b) testing the effect of the drug on the lateral motility of the cells;
(c) testing the effect of the drug on the transverse migration of the cells; and
(d) testing the effect of the drug on the invasiveness of the cells, namely the ability of the cells to move through a medium which is consumed by the cells.

As more fully described below, experiments carried out in connection with this invention have shown that administering ranolazine or riluzole at various dosage levels can increase the adhesiveness of the cells and/or reduce one or more of the lateral motility, transverse migration and invasiveness of the cells.

Accordingly, in accordance with another aspect of the invention, a compound, composition or other substance is provided which is used or intended to be used, in an appropriate dose, to inhibit or reduce the persistent part of the VGSC in metastatic cancer cells whilst leaving the transient part unaffected or only partially reduced, for inhibiting or reducing metastasis, preferably without directly causing cell death.

The advantages that flow from the invention, at least in certain aspects or forms, are:
(a) that breast and prostate cancer (and other cancers in which VGSCs are expressed) can be contained so that the patient may be able to live with such cancer without serious detriment;
(b) as a result, the need for the patient to undergo aggressive treatments to destroy the cancerous cells, such as by chemo or radiotherapy may be avoided;
(c) if a patient is suspected of having breast or prostate or other metastatic cancer, immediate treatment with appropriate doses of ranolazine or riluzole (or other substance with the relevant properties) can be given to inhibit or prevent metastasis whilst awaiting the results of definitive tests;
(d) the dosage necessary to achieve this only has to be high enough to inhibit the persistent part of the VGSC current;
(e) therapeutically acceptable doses of ranolazine or riluzole will achieve the required inhibition of the persistent part of these currents, whilst leaving the transient part substantially unaffected; and
(f) since ranolazine and riluzole have been on the market and approved for human use for many years, the invention can be put into clinical use without having to go through all the lengthy testing for side effects etc.

DETAILED DESCRIPTION

The invention is further described with reference to the accompanying drawings and experimental data set out below.

In the drawings:

FIG. 3 (b) is a sketch illustrating the effect of differing concentrations of ranolazine on the VGSC current components;

FIG. 3 (c) is a sketch illustrating the effect of differing concentrations of riluzole on the VGSC current components;

Figure 5:
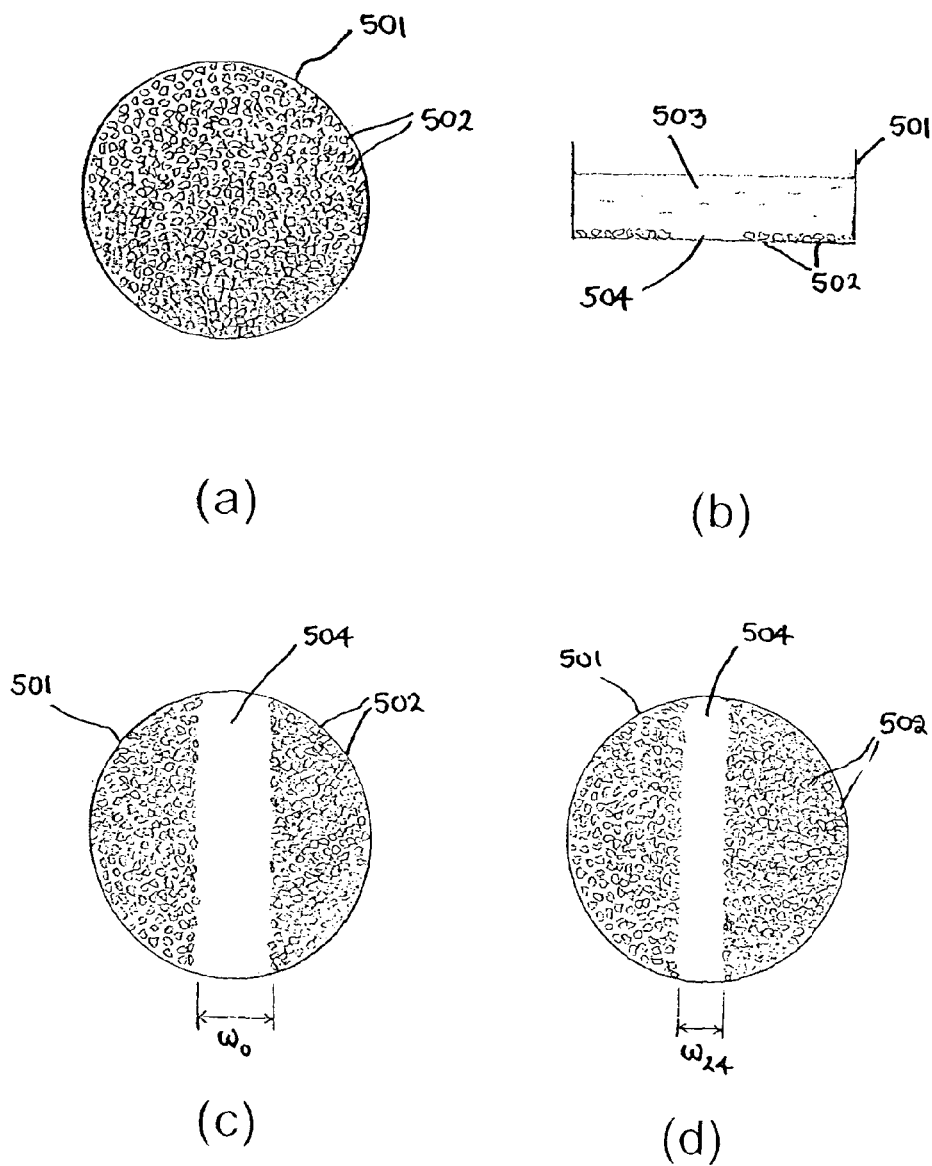
Figure 6:
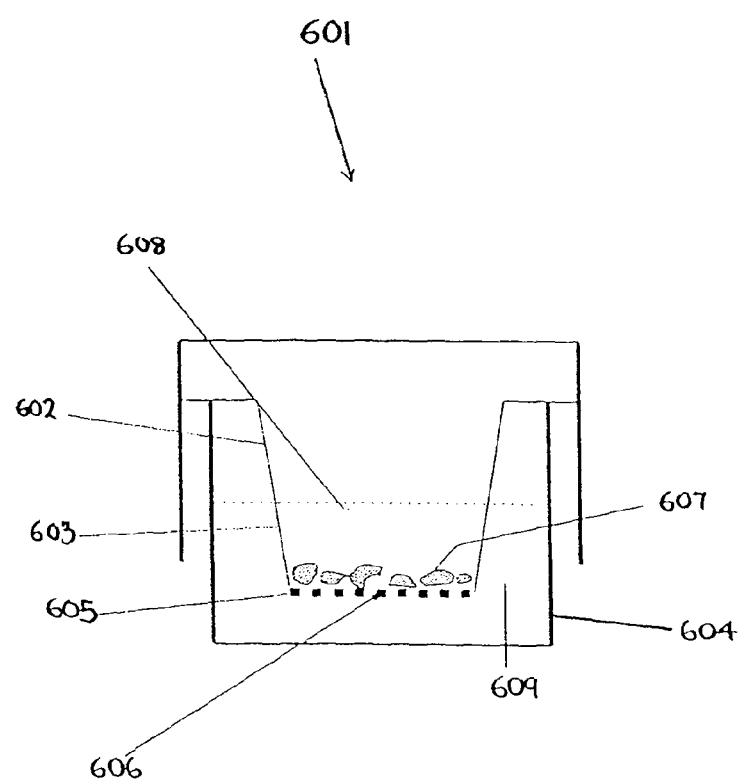
Figure 7:
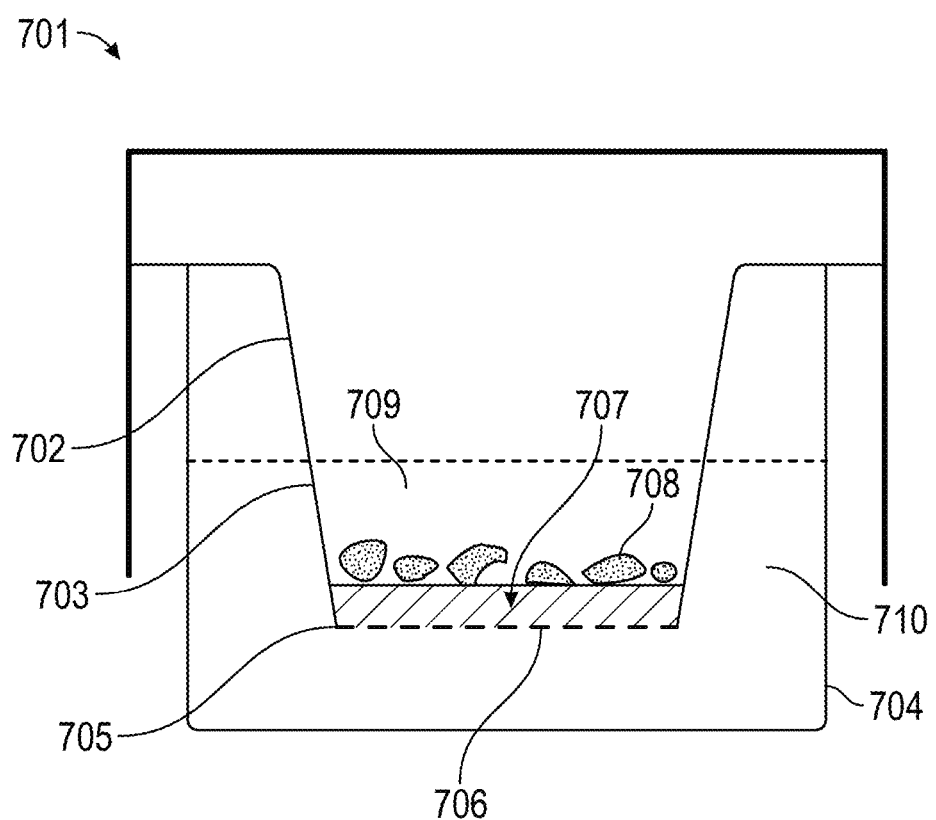
Figure 8:
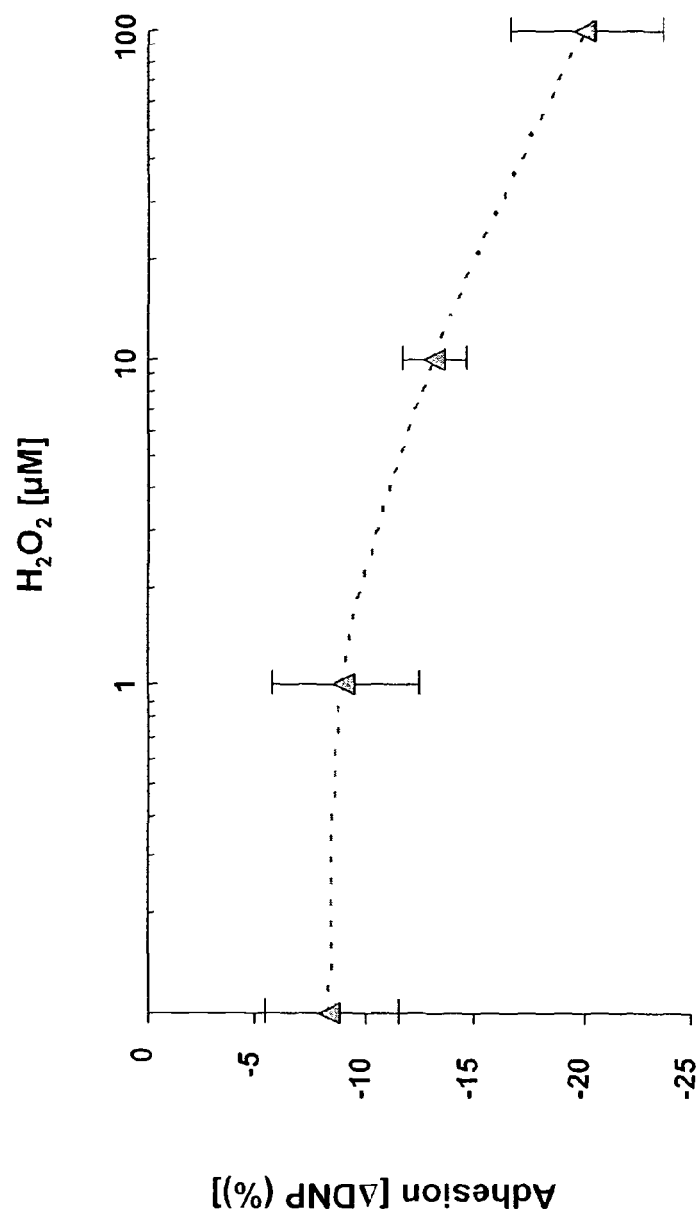
Figure 9:
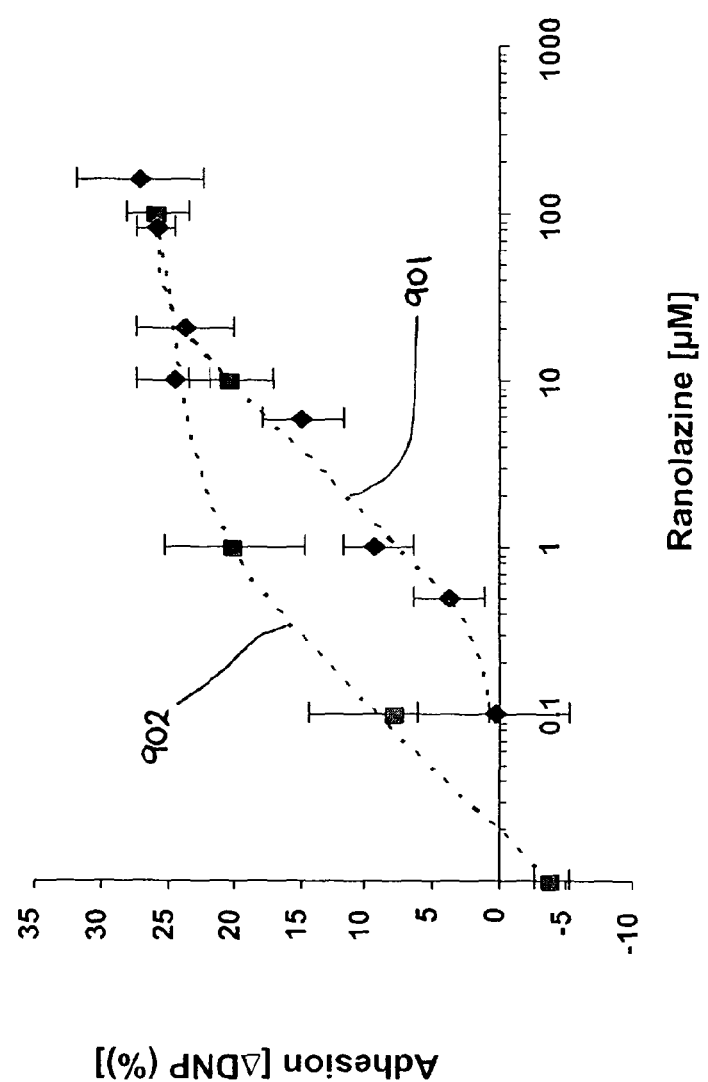
Figure 10:
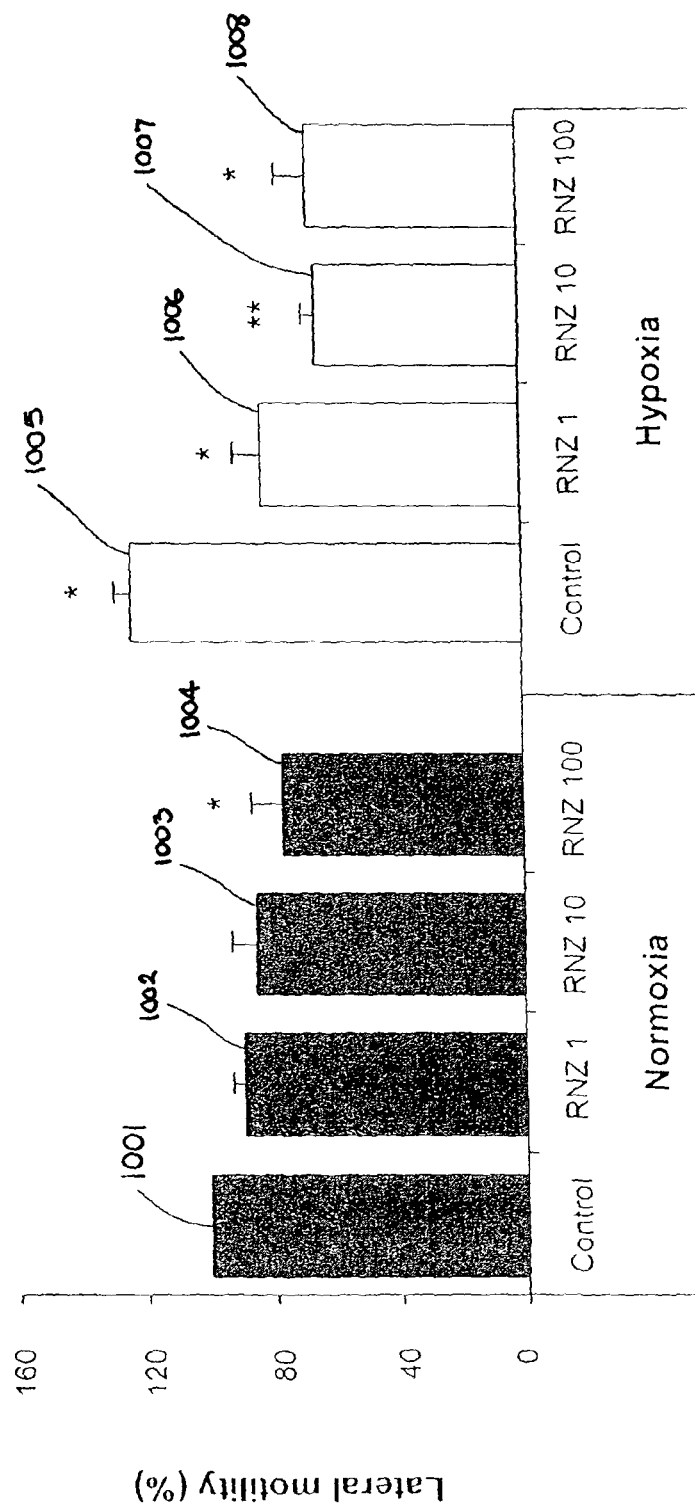
Figure 11:
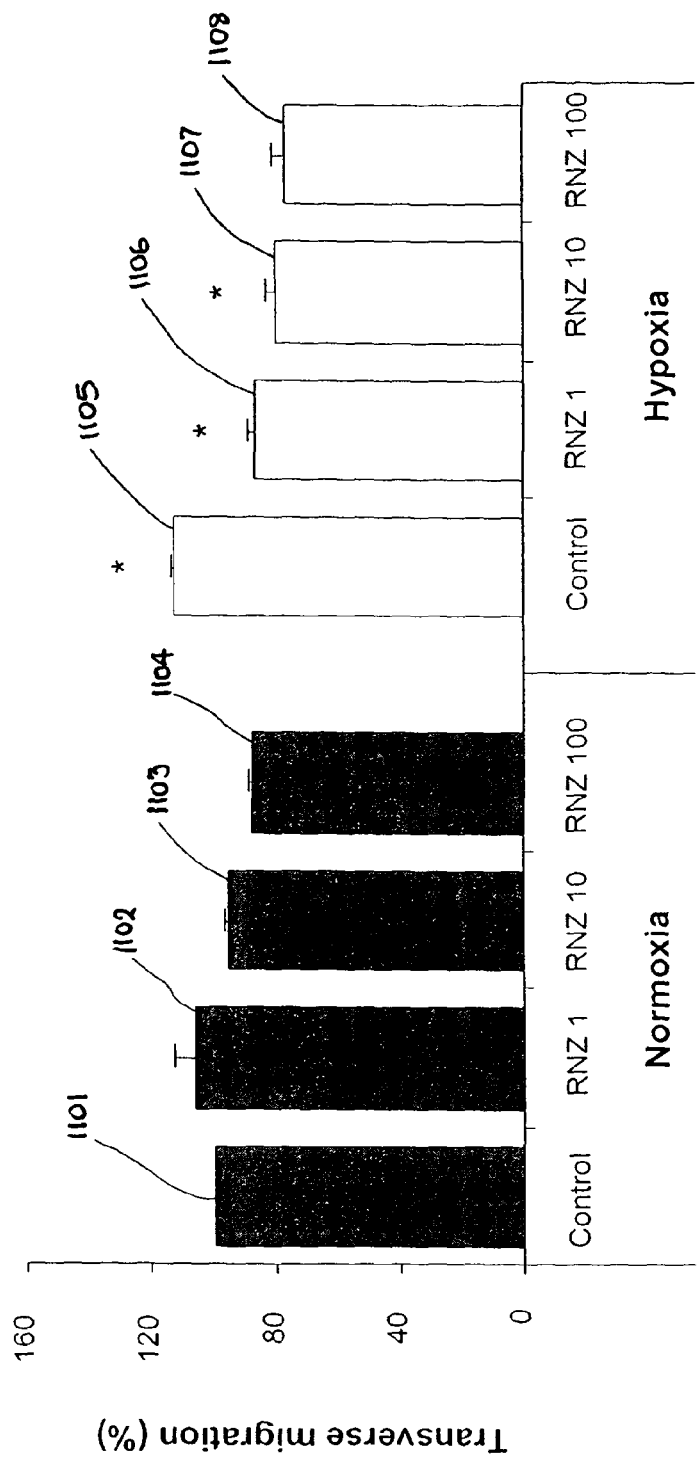
Figure 12:
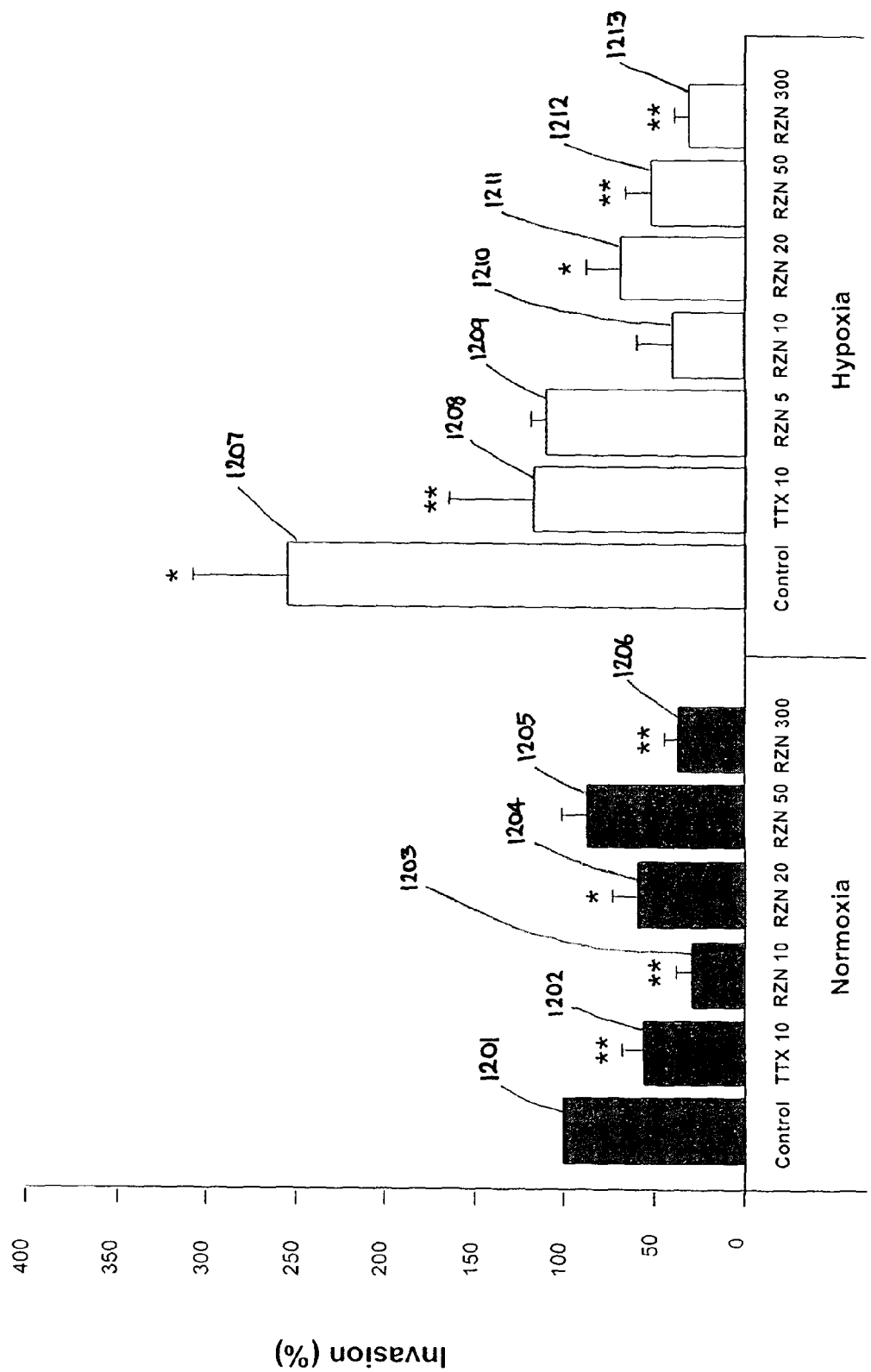
Figure 14:
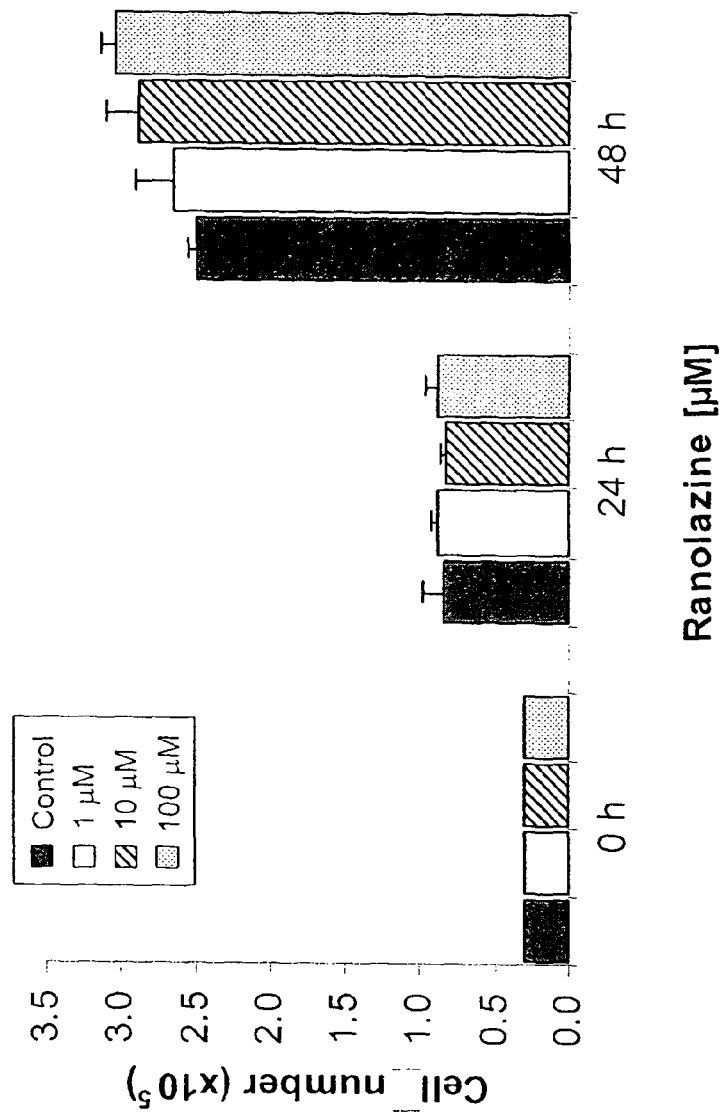
Figure 15:
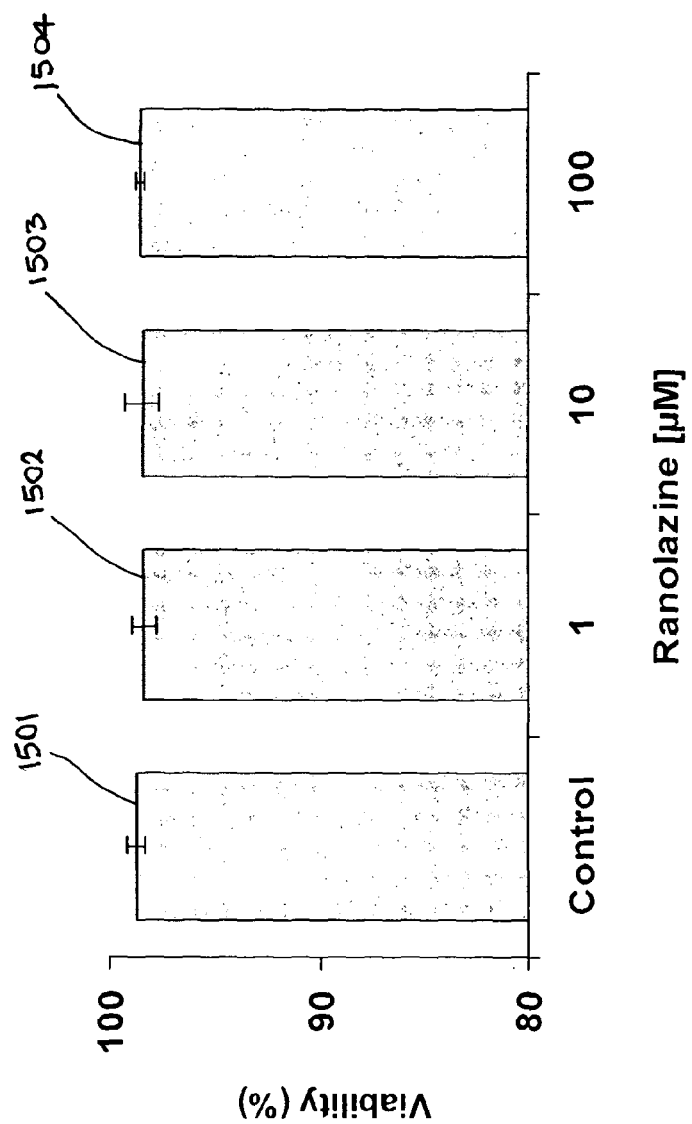
Figure 16:
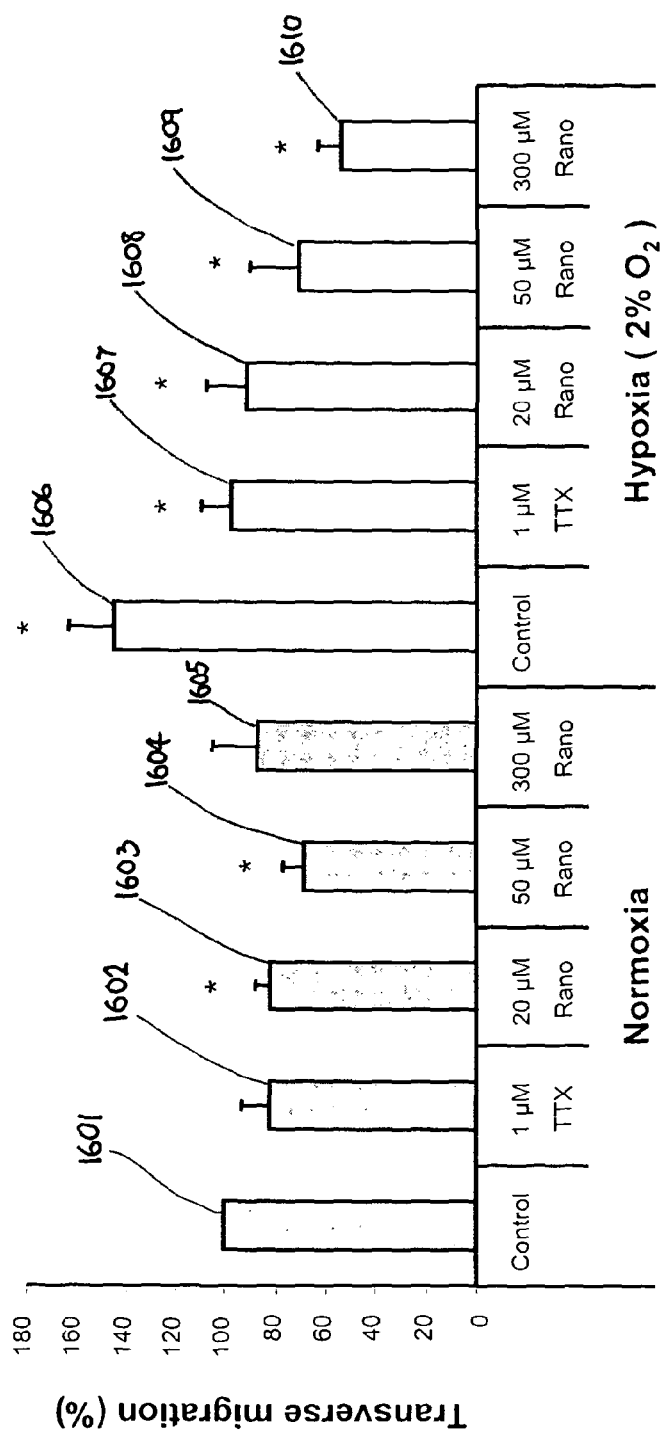
Figure 17:
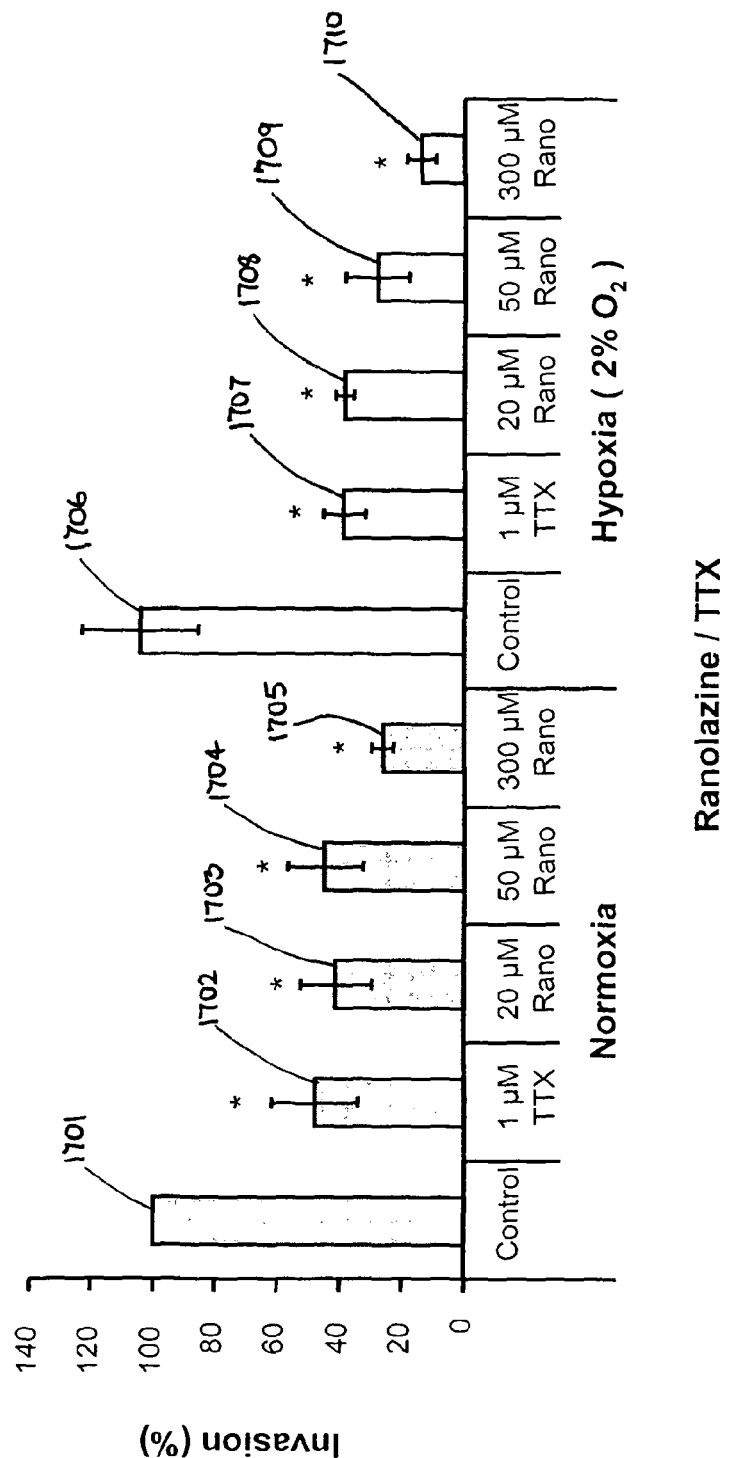
Figure 18:
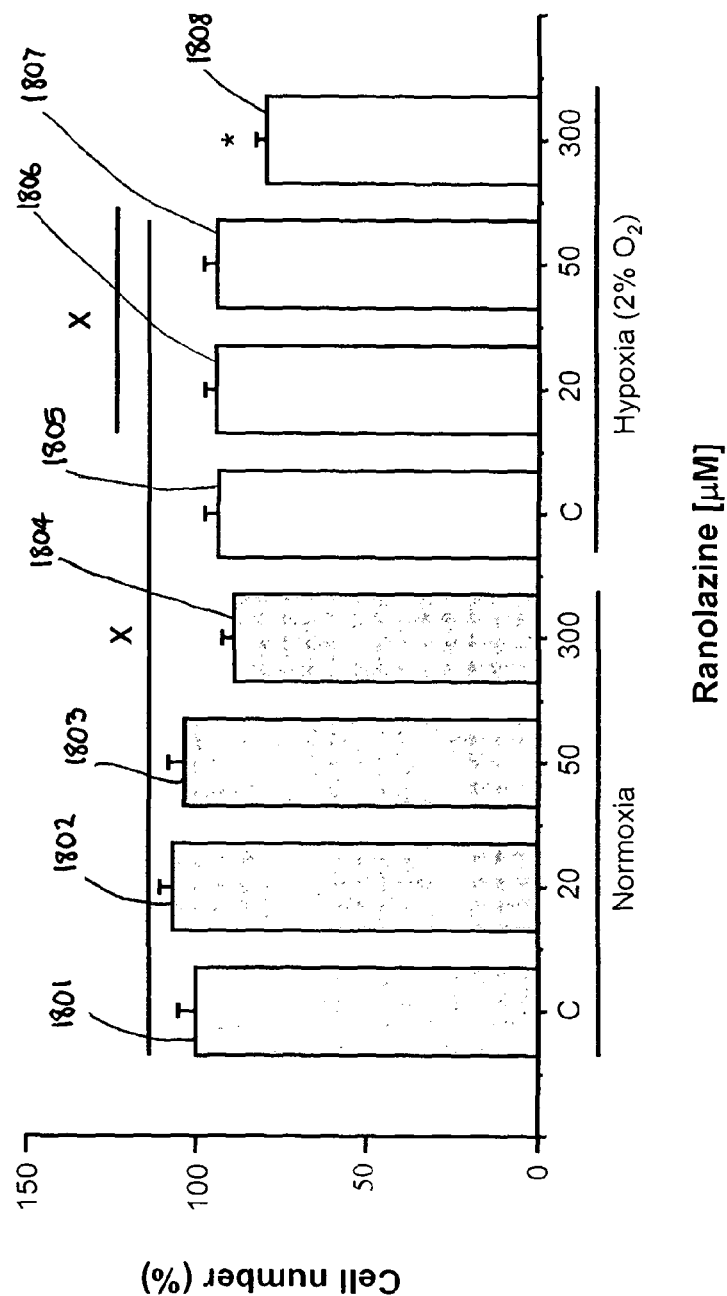
Figure 19:
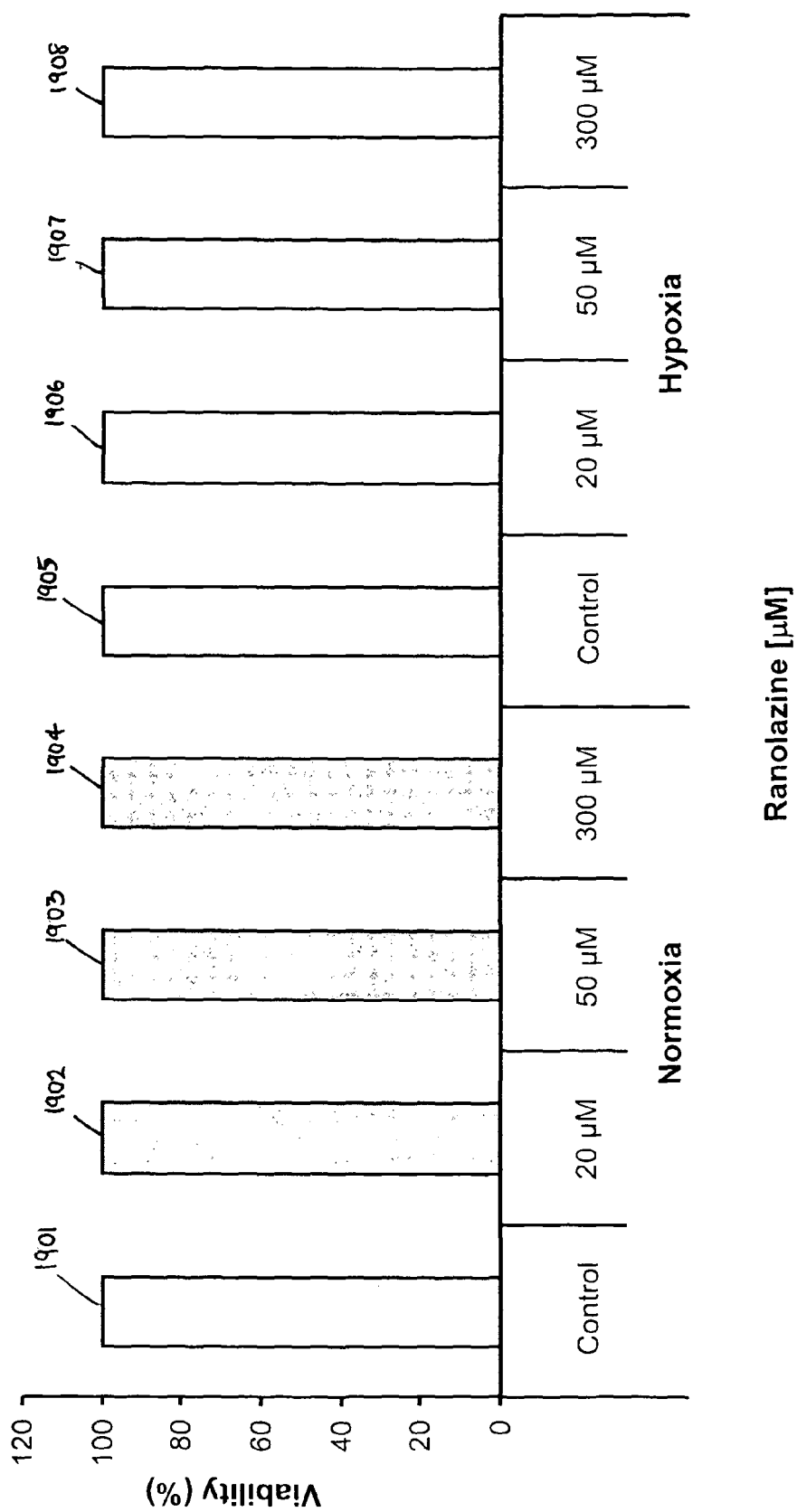
Figure 20:
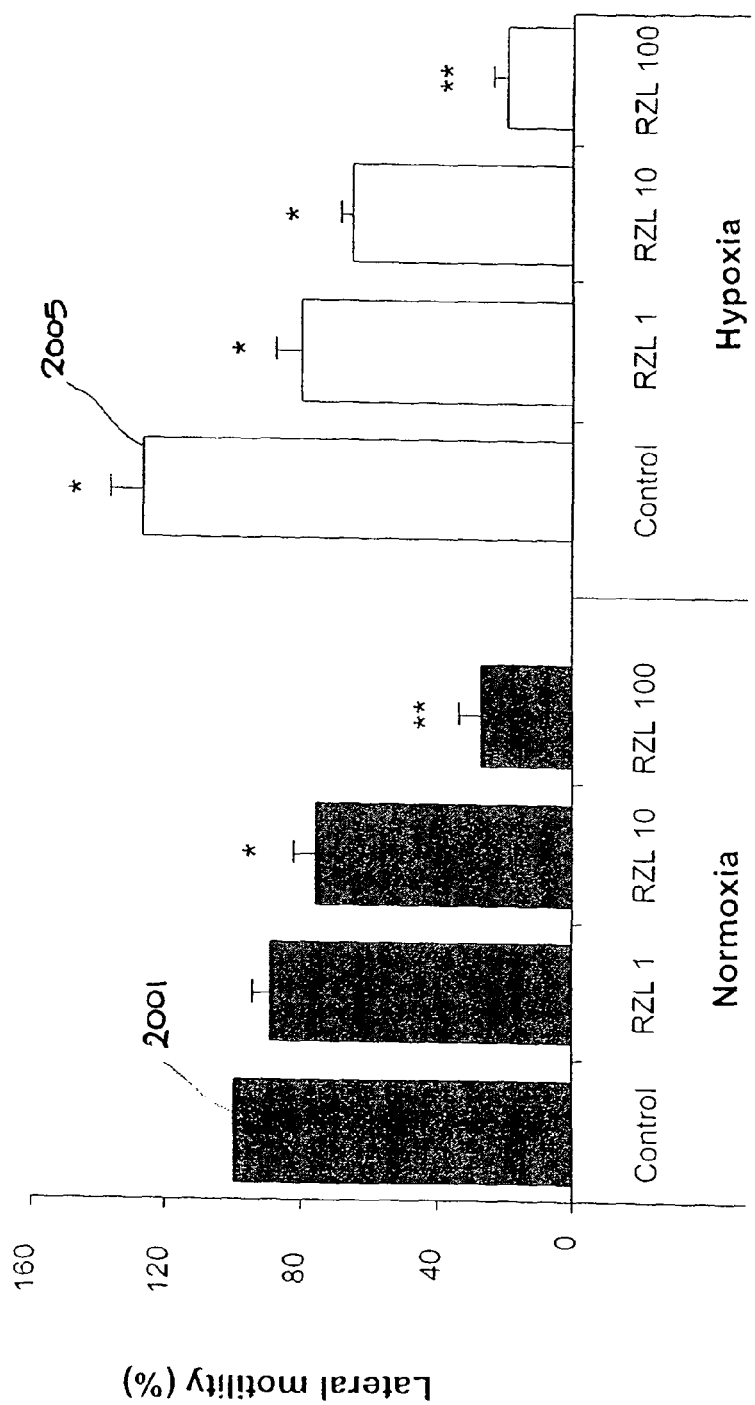
Figure 21:
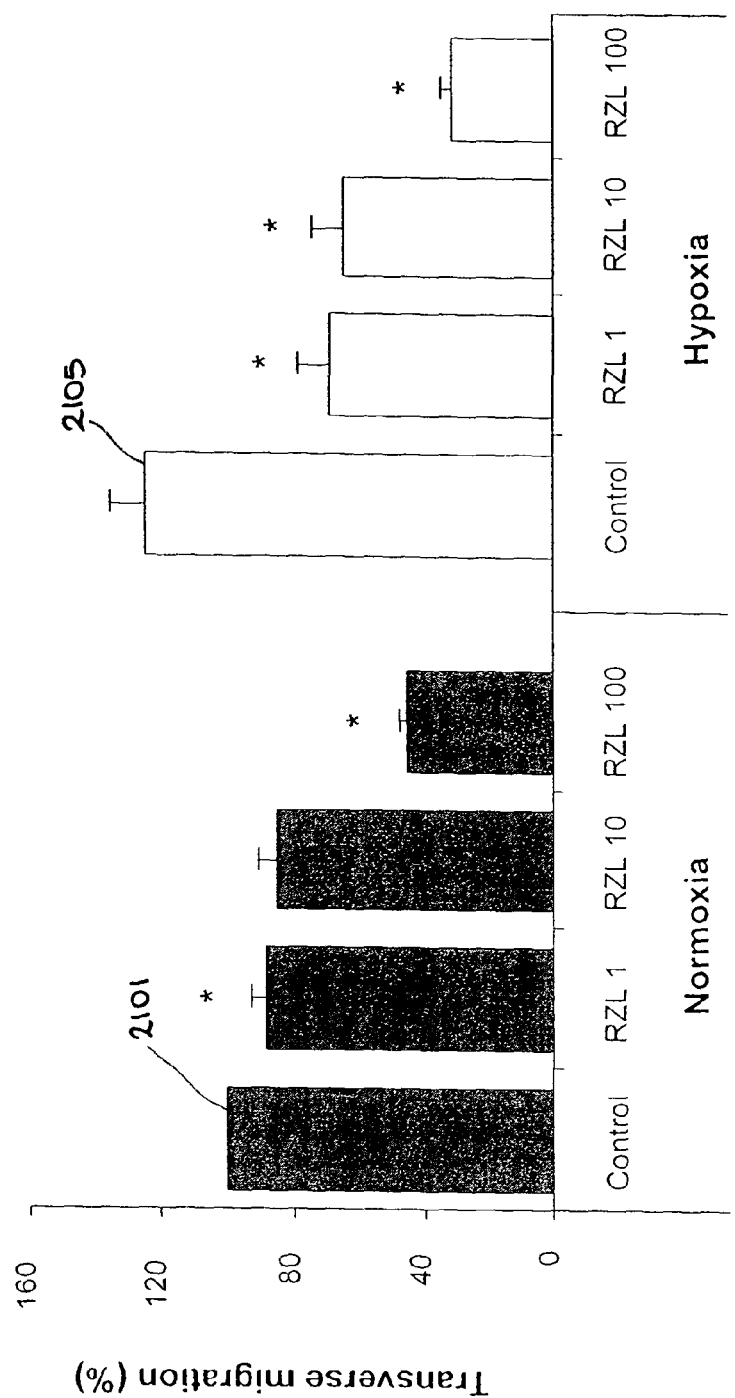
Figure 22:
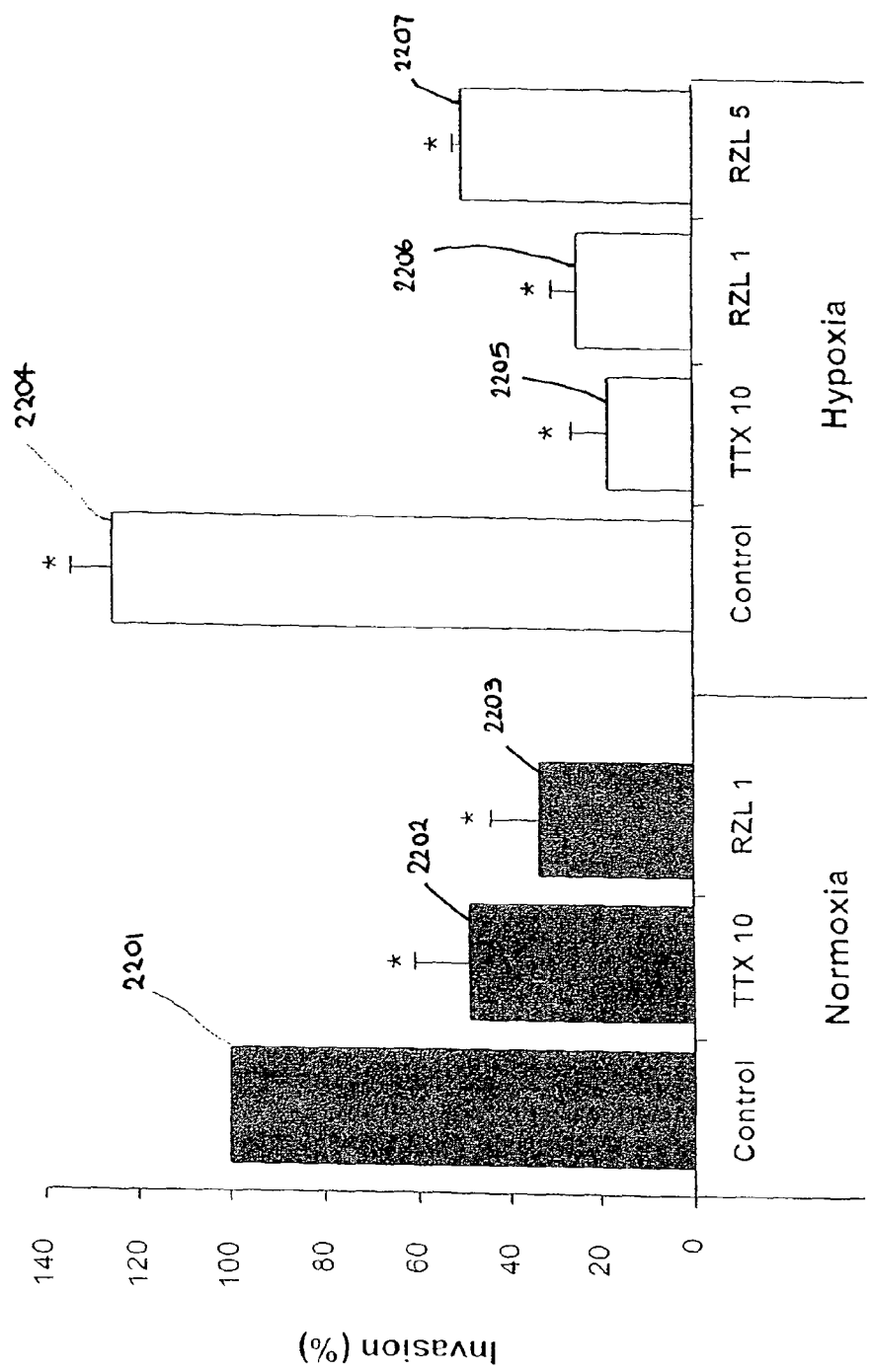
Figure 23:
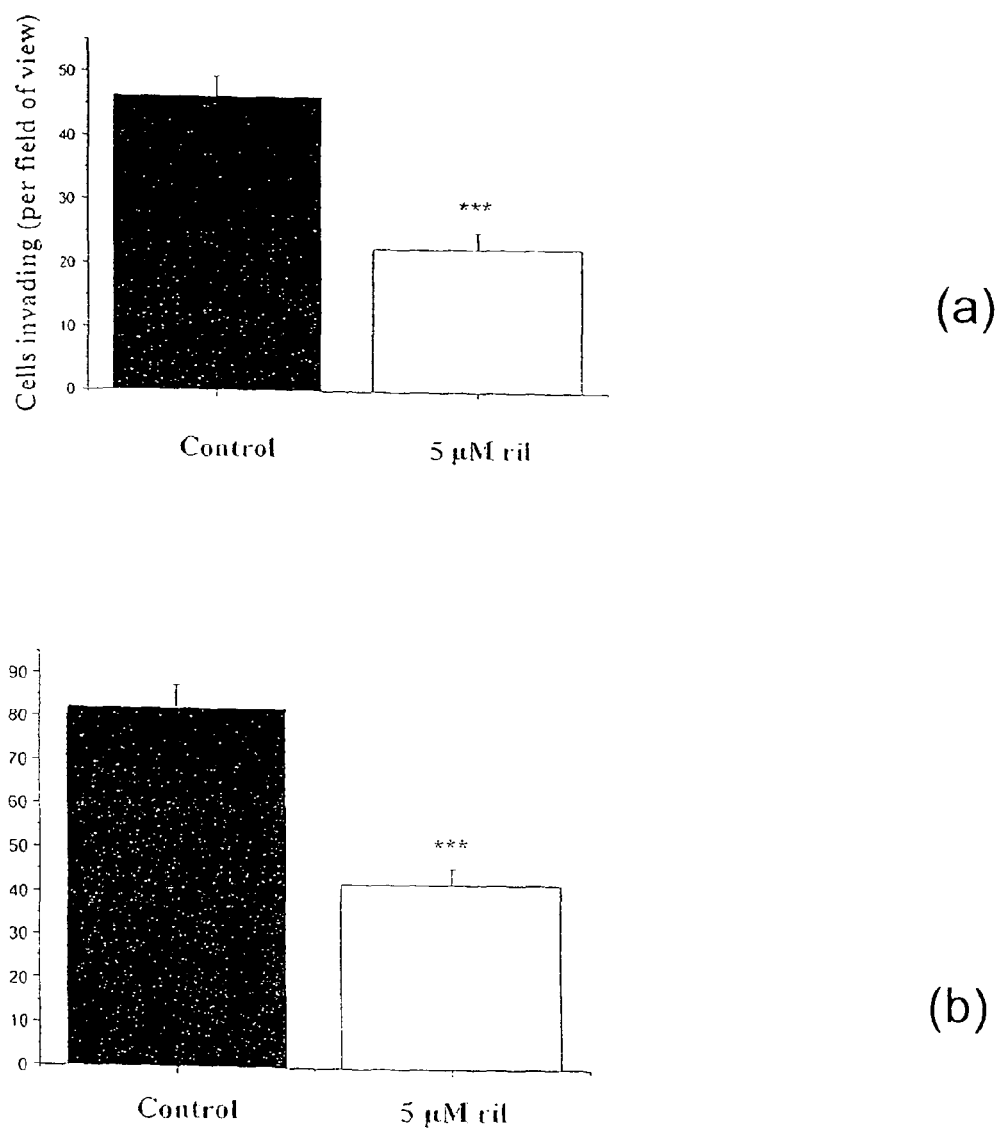
Figure 24:
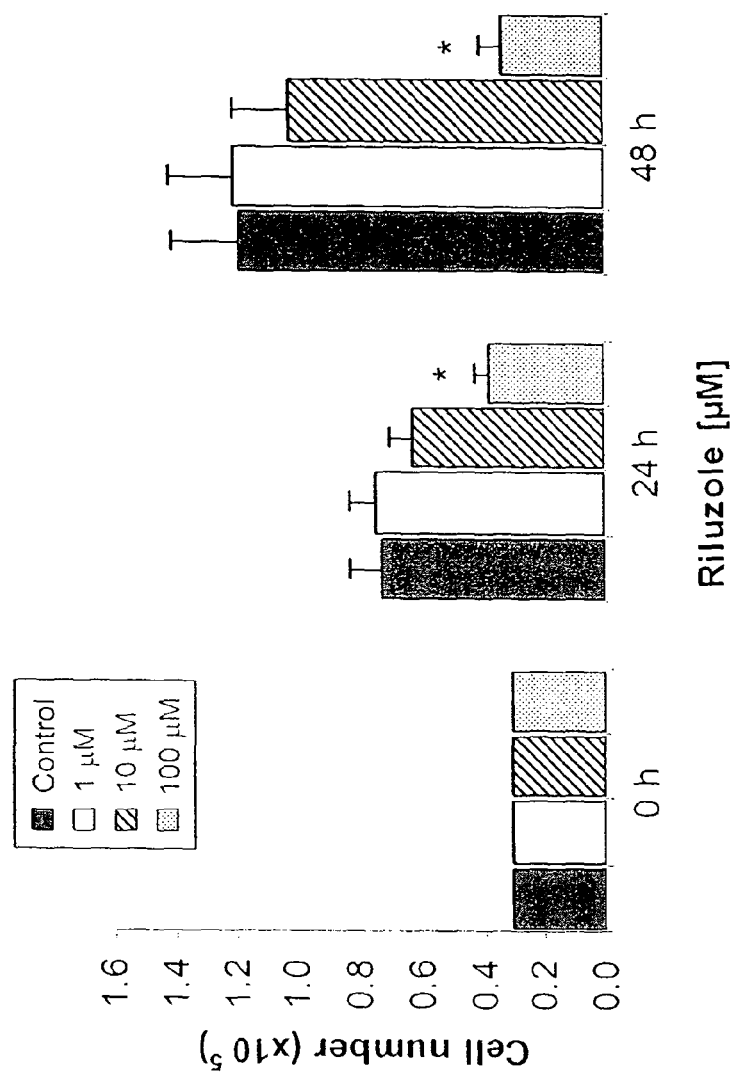
Figure 25:
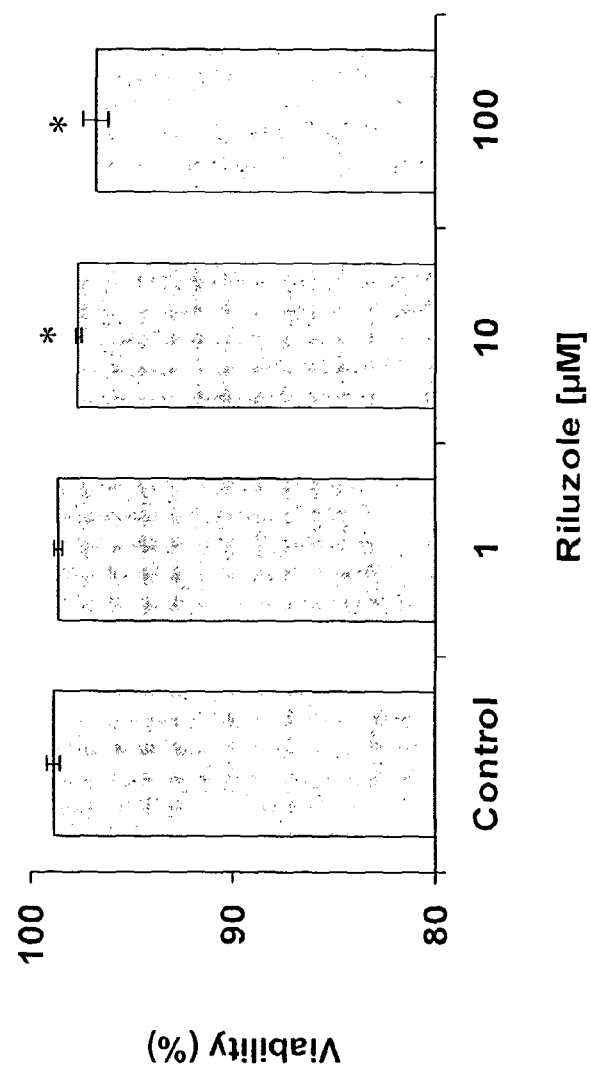
Figure 26:
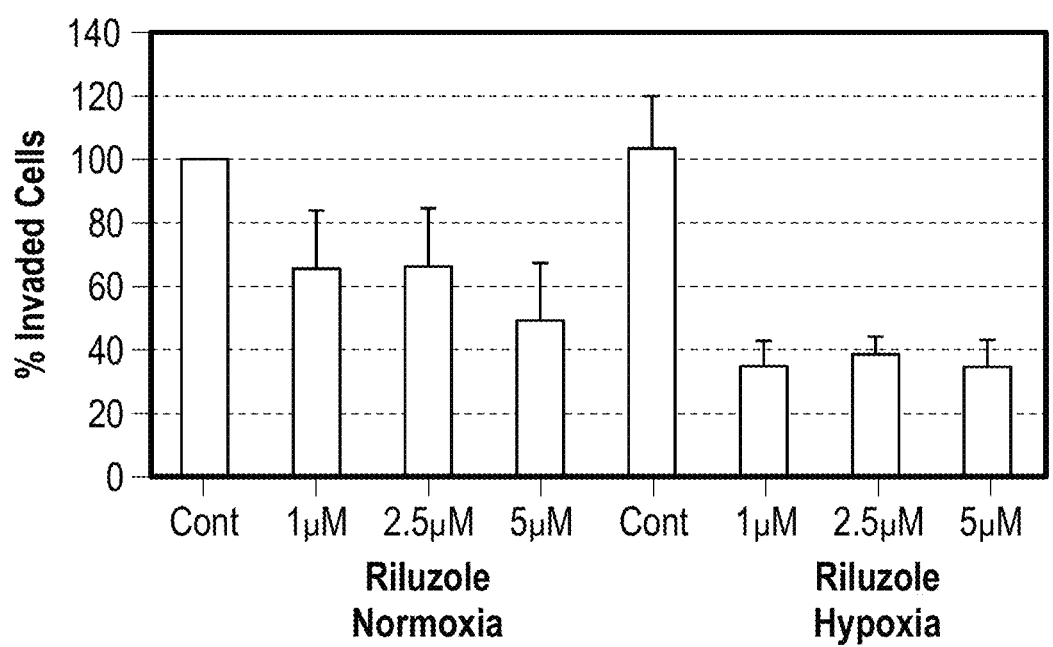
Figure 27:
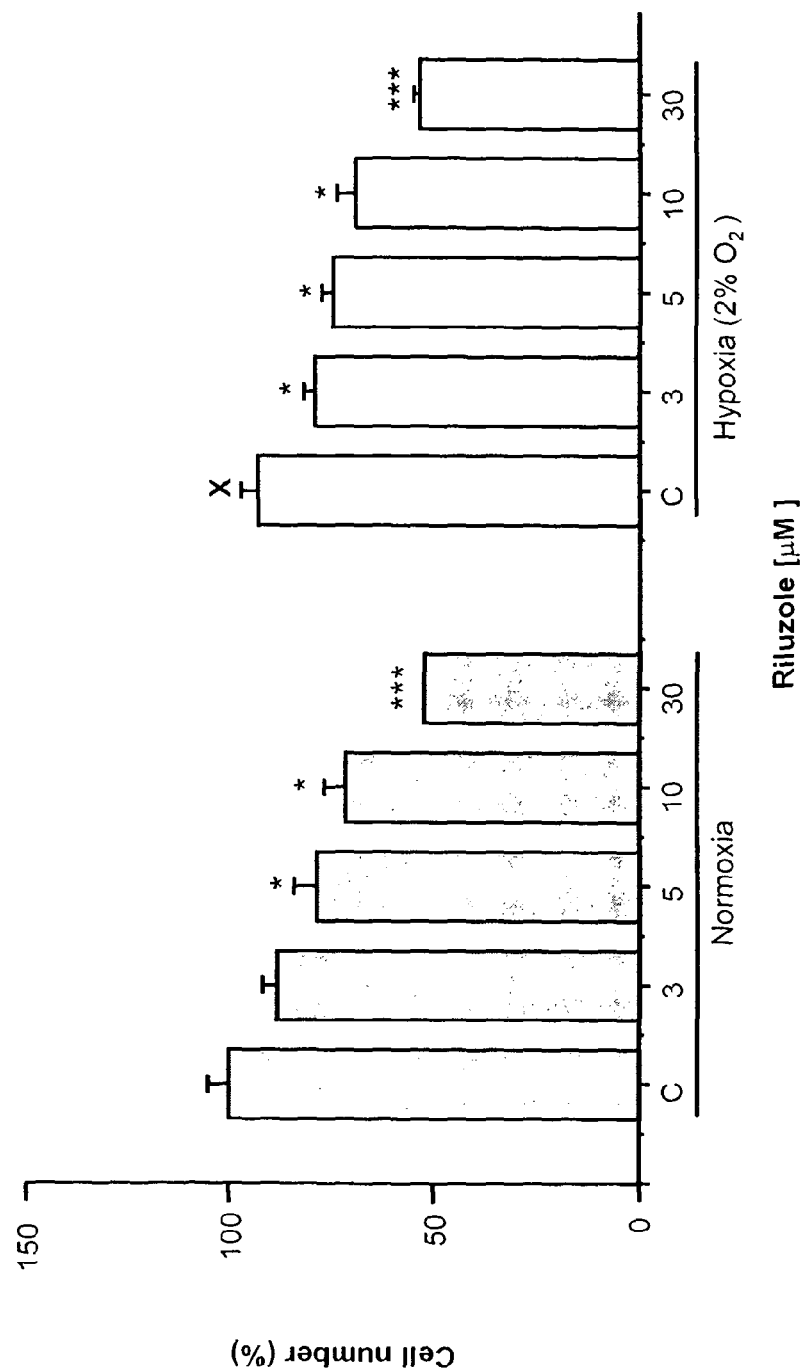
Figure 28:
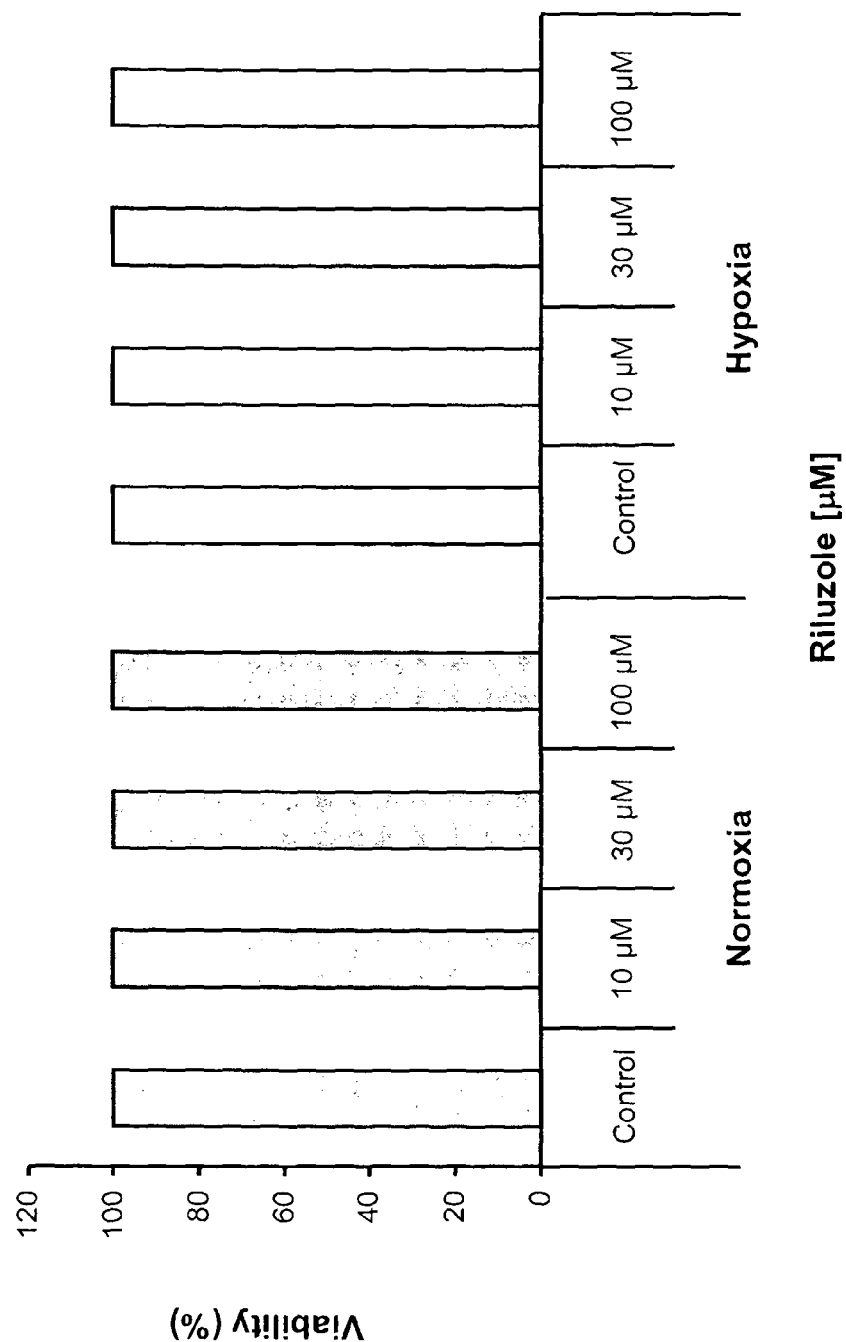

FIG. 5 is a schematic illustration of apparatus used for measuring the lateral motility of cells; view (a) is a plan view from above of a cell culture dish containing a semi-confluent layer of cells; view (b) is a schematic side sectional view of the plated cells; view (c) is a plan view of the plated cells at time t=zero when a scar has been created through the layer of cells, and view (d) is a plan view of the plated cells at a later time (t=24 hours) after the cells have moved and the wound has partially closed;

FIG. 6 is a schematic side sectional view of apparatus used for measuring the transverse migration of cells;

FIG. 7 is a schematic side sectional view of apparatus used for measuring the invasiveness of cells;

FIG. 8 is a graph showing the concentration dependent effect of induced chemical hypoxia on the single-cell adhesion of human metastatic breast cancer MDA-MB-231 cells;

FIG. 9 is a graph showing the dose-dependent effect of ranolazine on the single-cell adhesion of MDA-MB-231 cells under normoxia and chemically induced hypoxia;

FIG. 10 is a histogram showing the dose-dependent effects of ranolazine on the lateral motility of MDA-MB-231 cells under normoxia and hypoxia;

FIG. 11 is a histogram showing the dose-dependent effect of ranolazine on the transverse migration of MDA-MB-231 cells under normoxia and hypoxia;

FIG. 12 is a histogram showing the dose-dependent effect of ranolazine on the invasiveness of MDA-MB-231 cells under normoxia and hypoxia;

FIG. 13 is a series of histograms showing the dose-dependent effect of ranolazine on the invasiveness of MDA-MB-231 cells that have been pre-treated with ranolazine for different durations under hypoxia; view (a) is a histogram showing the effect of 5 μM ranolazine for cells treated only for 24 hours during the assay (i.e., no pre-treatment); view (b) is a histogram showing the effect of 5 μM ranolazine for cells pre-treated with the drug for 72 hours; view (c) is a histogram showing the effect of 25 μM ranolazine for cells treated only for 24 hours during the assay (i.e., no pre-treatment); view (d) is a histogram showing the effect of 5 μM ranolazine for cells pre-treated with the drug for 48 hours, and view (e) is a histogram showing the effect of 5 μM ranolazine for cells pre-treated with the drug for 72 hours;

FIG. 14 is a series of histograms showing lack of effect of ranolazine on the growth of MDA-MB-231 cells under normoxia;

FIG. 15 is a histogram showing the lack of effect of ranolazine on the viability of MDA-MB-231 cells under normoxia;

FIG. 16 is a histogram showing the dose-dependent effect of ranolazine on the transverse migration of rat strongly metastatic prostate cancer Mat-LyLu cells under normoxia and hypoxia;

FIG. 17 is a histogram showing the dose-dependent effect of ranolazine on the invasiveness of Mat-LyLu cells under normoxia and hypoxia;

FIG. 18 is a histogram showing the lack of effect of ranolazine on the proliferation of Mat-LyLu cells under normoxia and hypoxia;

FIG. 19 is a histogram showing the lack of effect of ranolazine on the viability of Mat-LyLu cells under normoxia and hypoxia;

FIG. 20 is a histogram showing the dose-dependent effect of riluzole on the lateral motility of MDA-MB-231 cells under normoxia and hypoxia;

FIG. 21 is a histogram showing the dose-dependent effect of riluzole on the transverse migration of MDA-MB-231 cells under normoxia and hypoxia;

FIG. 22 is a histogram showing the dose-dependent effect of riluzole on the invasiveness of MDA-MB-231 cells under normoxia and hypoxia;

FIG. 23 is 'a pair of histograms showing the comparative effect on the invasiveness of MDA-MB-231 pre-treated with 5 µM riluzole for >72 hours under hypoxia; view (a) is a histogram showing the effect of 5 µM riluzole for cells treated only for 24 hours during the assay (i.e., no pre-treatment); view (b) is a histogram showing the effect of 5 µM riluzole for cells pre-treated with the drug for 72 hours;

FIG. 24 is a histogram showing the dose-dependent effect of riluzole on the growth of MDA-MB-231 cells under normoxia;

FIG. 25 is a histogram showing the dose-dependent effect of riluzole on the viability of MDA-MB-231 cells under normoxia;

FIG. 26 is a histogram showing the dose-dependent effect of riluzole on the invasiveness of Mat-LyLu cells under normoxia and hypoxia;

FIG. 27 is a histogram showing the dose-dependent effect of riluzole on the growth of Mat-LyLu cells under normoxia and hypoxia, and FIG. 28 is a histogram showing the dose-dependent effect of riluzole on the viability of Mat-LyLu cells under normoxia and hypoxia.

Figure 1:
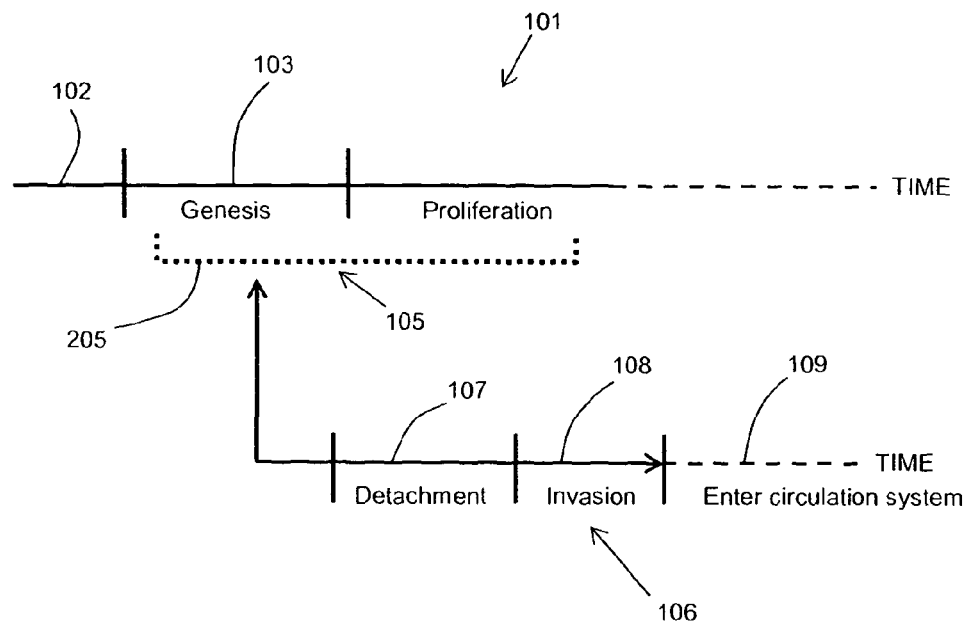
FIG. 1 is a schematic representation of a timeline for cancer progression from primary tumorigenesis to formation of secondary tumours (metastases)

With reference to FIG. 1, timeline 101 is a representation of three successive phases in the development of a tumour, namely a phase 102 prior to the development of cancerous cells, a phase 103 following phase 102 during which the genesis of cancer cells takes place and a phase 104, following phase 103, during which the cancerous cells proliferate so as to form a growing tumour. The proliferation phase 104 may begin soon after the genesis phase 103 begins.

It has been established that human breast and human prostate cancer cells may initially not include any functional VGSCs and that, unless such channels are expressed in the tumour, the tumour cells will not be invasive. However, in many such tumours, even though initially there are no VGSC's, at some point functional VGSC's will be expressed. This triggers a change to a condition in which the tumour may spread. FIG. 1 represents a situation in which initially the cells do not contain any functional VGSC's but at some point in time 105 the expression of functional VGSC begins. This may occur at any time after commencement of the genesis phase 103.

Timeline 106 in FIG. 1 illustrates the phases which arise following time 105, when the cancer becomes metastatic.

In the first phase 107 following time 105, metastatic cells detach themselves from the tumour. Thereafter, in phase 108, they invade and move through surrounding tissue in the same organ towards the circulation system, in particular the vascular and/or the lymphatic system. In phase 109, the metastatic cells enter the circulation system which may then carry them to other organs in the body, at which they may cause the formation of secondary tumours.

Figure 2:
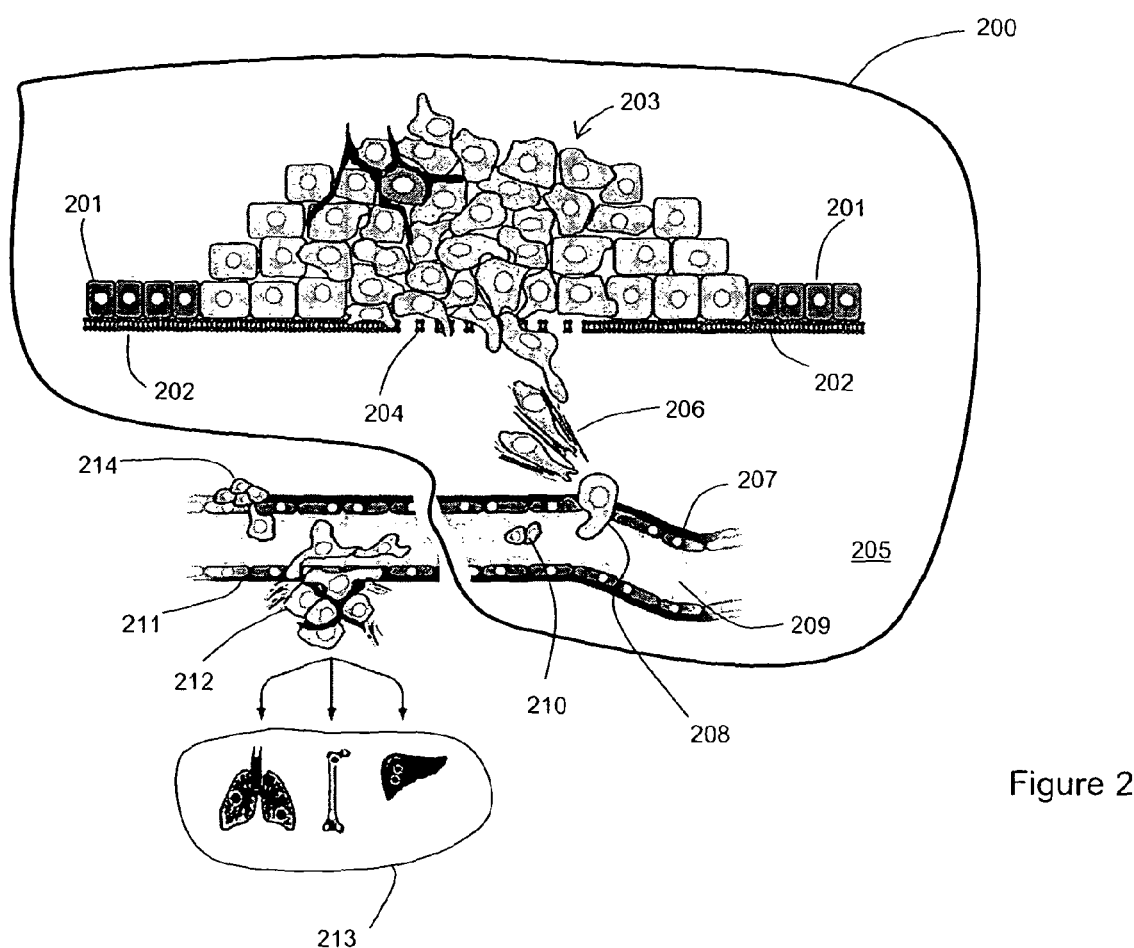
FIG. 2 is a schematic illustration of the cellular processes occurring during cancer initiation and progression to metastasis.

The above phases are pictorially represented in FIG. 2 in which reference number 200 represents a portion of an organ such as a breast or a prostate. Healthy cells 201 of the breast or prostate are shown as supported on a basement membrane 202 and surrounding a cancerous tumour 203, which is assumed to have gone through the genesis phase 103 and into the proliferation phase 104.

Certain cells 204 of the cancerous tumour 202 are shown as detaching from the tumour 203 and passing through a degraded region 202a of the basement membrane 202 into adjacent region 205 of the organ containing the tumour 203, which region may comprise mainly collagen fibres. Cancer cells 206, which have become detached from the tumour and have passed through the basement membrane 202, are shown passing through the region 205 towards a blood vessel 207. A cancerous cell 208 is shown migrating through the wall of the blood vessel 207 into the bloodstream 209.

Cells 210, which have already entered the bloodstream, are shown as being carried within the bloodstream to a region 211 where cells 212 are shown as having migrated outwardly through the wall of the blood vessel 207 towards another organ 213, such as the lymph glands or liver, in which they may form a secondary tumour (not shown).

Reference number 214 represents dormant cancerous cells which have simply settled in or adjacent to the wall of the blood vessel 207.

As more fully explained below, the invention provides a treatment or means for preventing or reducing one or more of the metastatic behaviours of the cancer cells which takes place in the various phases described. In particular, the invention provides a treatment or means for:

(a) increasing the adhesiveness of the cells in the tumour so that they are less likely to detach; and/or (b) reducing the motility of the cells which have become detached so they are less likely to move to and through the basement membrane into the surrounding tissue; and/or (c) reducing the invasiveness of the cells which have entered the surrounding tissue by reducing their ability to move through that tissue towards the circulation system; and/or (d) reducing the ability of the cells to migrate from that tissue into the circulatory system via the walls thereof.

It has been explained above that cancerous cells which do not have functional VGSCs expressed therein do not behave invasively. Further, it is known that current passes through VGSCs in pulses, each of which comprises a transient or peak part followed by a much lower level persistent or late part. In accordance with an aspect of the invention, one or more of the above metastatic behaviours is inhibited or reduced by inhibiting or reducing the persistent part of the current whilst not eliminating the peak part, so making it possible to use a drug which will preferentially reduce the persistent part of the current.

Some such drugs are known for treating heart conditions such as arrhythmia or angina. In the case of treating the heart, it is vital to ensure that the peak part of the current is not eliminated because this is essential to maintain the functionality of the heart and its rhythm. Thus, in accordance with an aspect of the invention a known drug, such as ranolazine or riluzole, previously used for inhibiting or reducing the persistent part of the VGSC current without eliminating the peak part is used for inhibiting or reducing metastatic behaviour in cancer, especially breast or prostate cancer.

The nature of the VGSC current, and the effect on it of treatment with ranolazine or riluzole, will be further described with reference to FIGS. 3(a), 3(b) and 3(c).

Figure 3:
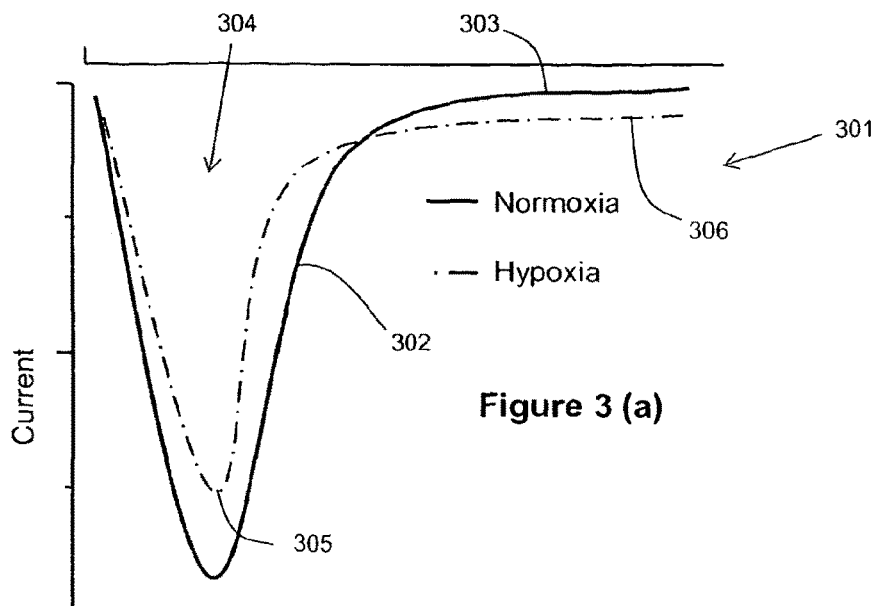
FIG. 3 (a) is a sketch illustrating the current through VGSC's, showing both the transient and persistent parts of the current and also showing the current under both normoxic and hypoxic conditions.
Figure 3:
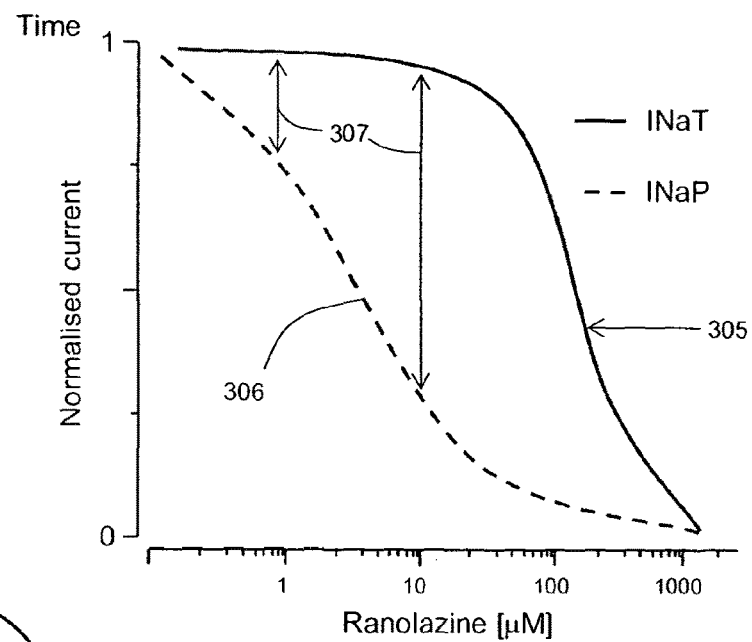
Figure 3:
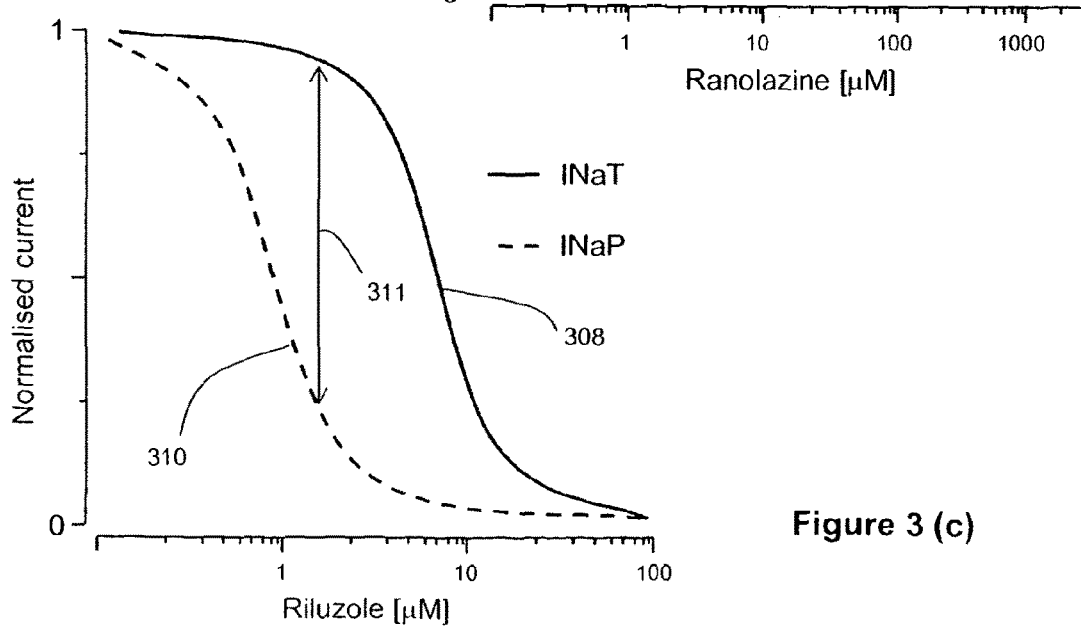

Referring to FIG. 3(a), curve 301, shown as an unbroken line, represents a current pulse flowing through functional VGSC under normoxic conditions, the horizontal axis being time and the vertical axis being amplitude or magnitude of the current. As can be seen, this current pulse comprises a peak or transient portion 302 and the persistent or late portion 303. In practice, the time period for which the persistent part 303 persists is very much greater than the time period of the transient part 302 although, since FIG. 3(a) is a diagrammatic sketch rather than a curve actually obtained from experimental data, this is not shown in the figure.

Curve 304, drawn in chain dotted lines, shows a pulse of VGSC current under hypoxic conditions. As can be seen, the peak part 305 of the current under hypoxic conditions is smaller than the peak part 301 under normoxic conditions, but the persistent part 306 under hypoxic conditions is greater than the persistent part 303 under normoxic conditions. The difference between these curves under hypoxic and normoxic conditions is relevant, as will become clear from consideration of experimental results which are described below, because many of the cells in a cancerous tumour are hypoxic due to their partial isolation, by other cancerous cells, from the blood circulation system.

FIG. 3(b) is a sketch illustrating the effect of increasing doses of ranolazine on the transient and persistent parts of the VGSC current respectively. As can be seen, the horizontal axis represents the dosage level of ranolazine and the vertical axis represents the normalised VGSC current. Solid line curve 305 represents the magnitude of the transient part of the current plotted against increasing dosage and broken line curve 306 represents the magnitude of the persistent part of the current against increasing dosage of ranolazine, dosage levels being indicated on the horizontal axis.

It can be further seen from FIG. 3(b) that at dosage levels in the range 1 to 10 μM, which are therapeutically acceptable to human beings, the persistent part of the current is reduced significantly more than the transient part. The difference between the two reductions is indicated in FIG. 3(b) by the double headed arrows 307.

A similar effect with increasing doses of riluzole can be seen from FIG. 3(c), in which solid line curve 308 represents the magnitude of the transient part of the current plotted against increasing doses of riluzole and the broken line curve 310 represents the magnitude of the persistent part of the current. Therapeutically acceptable doses of riluzole for human beings include the range from 1 μM to 10 μM. As can be seen in FIG. 3(c), and as represented by double headed arrow 311, the reduction in the magnitude of the persistent part of the current is substantially more than the reduction in the magnitude of the transient part.

As with FIG. 3(a), the curves of FIGS. 3(b) and 3(c) are sketches to illustrate the currents rather than being based upon the specific experimental results.

Experiments which are fully described below have been conducted to measure the effects of various dosage levels of ranolazine and riluzole on one or more of the metastatic behaviours of certain cancerous cell lines. Specifically, in these experiments measurements of one or more of the adhesiveness of the cells, their lateral mobility, their invasiveness and their transverse migration have been made for each of these drugs at various dosage levels. Further, experiments have been conducted to determine the effect of some of these doses on the proliferative activity of the cells and on the viability of the cells (that is to say whether or not the drugs kill the cells).

Before describing the experiments and the quantitative results obtained from them, the following tables summarise qualitatively the results which have been obtained. It can be seen from these tables, and the subsequent detailed discussion of the experiments and the results obtained, that reduction in various metastatic behaviours can be achieved at therapeutically acceptable levels without affecting the proliferation of the cells and without killing the cells. The latter may be particularly important because it has recently been suggested that treating cancer by killing the cells may be counter-productive because, after the killing treatment has been discontinued, the cancer may reappear in more aggressive form. Preventing or reducing the invasiveness of the cancerous cells without killing them may therefore be a treatment which has considerable advantages over the conventional treatments of killing the cells.

Tables 1 and 2 summarise the results of experiments with various dosage levels of ranolazine on human breast cancer and rat prostate cancer cells (rat prostate cells being similar to human prostate cells). Tables 3 and 4 summarise the results obtained by treating cells of the same cell lines with various dosage levels of riluzole.

TABLE 1

BREAST CANCER (HUMAN MDA-MB-231) - RANOLAZINE [μM]

| CELL BEHAVIOUR | Hypoxia | | | | | Normoxia | | | | |
| --- | --- | --- | --- | --- | --- | --- | --- | --- | --- | --- |
| ADHESION | 0.1 μM increased | 1 μM increased | 10 μM decreased | 100 μM no benefit | | 0.5 μM increased | 1 μM increased | 10 μM increased | 20 μM increased | 100 μM increased |
| LATERAL MOTILITY | | 1 μM decreased | 10 μM decreased | 100 μM decreased | | | 1 μM decreased | 10 μM decreased | | 100 μM decreased |
| TRANSVERSE MIGRATION | | 1 μM decreased | 10 μM decreased | 100 μM decreased | | | 1 μM increased | 10 μM decreased | | 100 μM decreased |
| INVASIVENESS (no pretreatment) | 5 μM no benefit | 10 μM decreased | 20 μM no benefit | 25 μM decreased | 50 μM decreased | 300 μM decreased | 10 μM decreased | 20 μM decreased | 50 μM no effect | 300 μM decreased |
| INVASIVENESS (pretreatment) | 5 μM 72 hours decreased | | 25 μM 48 hours decreased | 25 μM 72 hours decreased | | | | | | |

TABLE 1-continued

BREAST CANCER (HUMAN MDA-MB-231) - RANOLAZINE [μM]

| CELL BEHAVIOUR | Hypoxia | | | Normoxia | | |
|---|---|---|---|---|---|---|
| PROLIFERATION (24 hours) | | | | 1 μM no effect | 10 μM no effect | 100 μM no effect |
| CELL VIABILITY | | | | 1 μM no effect | 10 μM no effect | 100 μM no effect |

TABLE 2

PROSTATE CANCER (RAT Mat-LyLu) - RANOLAZINE [μM]

| CELL BEHAVIOUR | Hypoxia | | | Normoxia | | |
|---|---|---|---|---|---|---|
| ADHESION | | | | | | |
| LATERAL MOTILITY | | | | | | |
| TRANSVERSE MIGRATION | 20 μM decreased | 50 μM decreased | 300 μM decreased | 20 μM decreased | 50 μM decreased | 300 μM no effect |
| INVASIVENESS (no pretreatment) | 20 μM decreased | 50 μM decreased | 300 μM decreased | 20 μM decreased | 50 μM decreased | 300 μM decreased |
| INVASIVENESS (pretreatment) | | | | | | |
| PROLIFERATION (24 hours) | 20 μM no effect | 50 μM no effect | 300 μM tail off | 20 μM no effect | 50 μM no effect | 300 μM tail off |
| CELL VIABILITY | 20 μM no effect | 50 μM no effect | 300 μM no effect | 20 μM no effect | 50 μM no effect | 300 μM no effect |

TABLE 3

BREAST CANCER (HUMAN MDA-MB-231) - RILUZOLE [μM]

| CELL BEHAVIOUR | Hypoxia | | | Normoxia | | |
|---|---|---|---|---|---|---|
| ADHESION | | | | | | |
| LATERAL MOTILITY | 1 μM decreased | 10 μM decreased | 100 μM decreased | 1 μM no effect | 10 μM decreased | 100 μM decreased |
| TRANSVERSE MIGRATION | 1 μM decreased | 10 μM decreased | 100 μM decreased | 1 μM decreased | 10 μM no effect | 100 μM decreased |
| INVASIVENESS (no pretreatment) | 1 μM decreased | 5 μM decreased | | 1 μM decreased | | |
| INVASIVENESS (pretreatment) | | 5 μM 72 hours decreased | | | | |
| PROLIFERATION (24 hours) | | | | 1 μM no effect | 10 μM no effect | 100 μM tail off |
| CELL VIABILITY | | | | 1 μM no effect | 10 μM cell death | 100 μM cell death |

TABLE 4

PROSTATE CANCER (RAT Mat-LyLu) - RILUZOLE [μM]

| CELL BEHAVIOUR | Hypoxia | | | Normoxia | | |
|---|---|---|---|---|---|---|
| ADHESION | | | | | | |
| LATERAL MOTILITY | | | | | | |
| TRANSVERSE MIGRATION | | | | | | |
| INVASIVENESS (no pretreatment) | 1 μM decreased | 2.5 μM decreased | 5 μM decreased | 1 μM decreased | 2.5 μM decreased | 5 μM decreased |

TABLE 4-continued

| PROSTATE CANCER (RAT Mat-LyLu) - RILUZOLE [μM] | | | | | | | | | | |
|---|---|---|---|---|---|---|---|---|---|---|
| CELL BEHAVIOUR | Hypoxia | | | | | Normoxia | | | | |
| INVASIVENESS (pretreatment) | | | | | | | | | | |
| PROLIFERATION (24 hours) | | 3 μM no effect | 5 μM tail off | 10 μM tail off | 30 μM tail off | | 3 μM tail off | 5 μM tail off | 10 μM tail off | 30 μM tail off |
| CELL VIABILITY | 1 μM no effect | | | 10 μM cell death | 30 μM cell death | 100 μM cell death | | | 10 μM no effect | 30 μM no effect | 100 μM no effect |

Single-Cell Adhesion Assay

Figure 4:
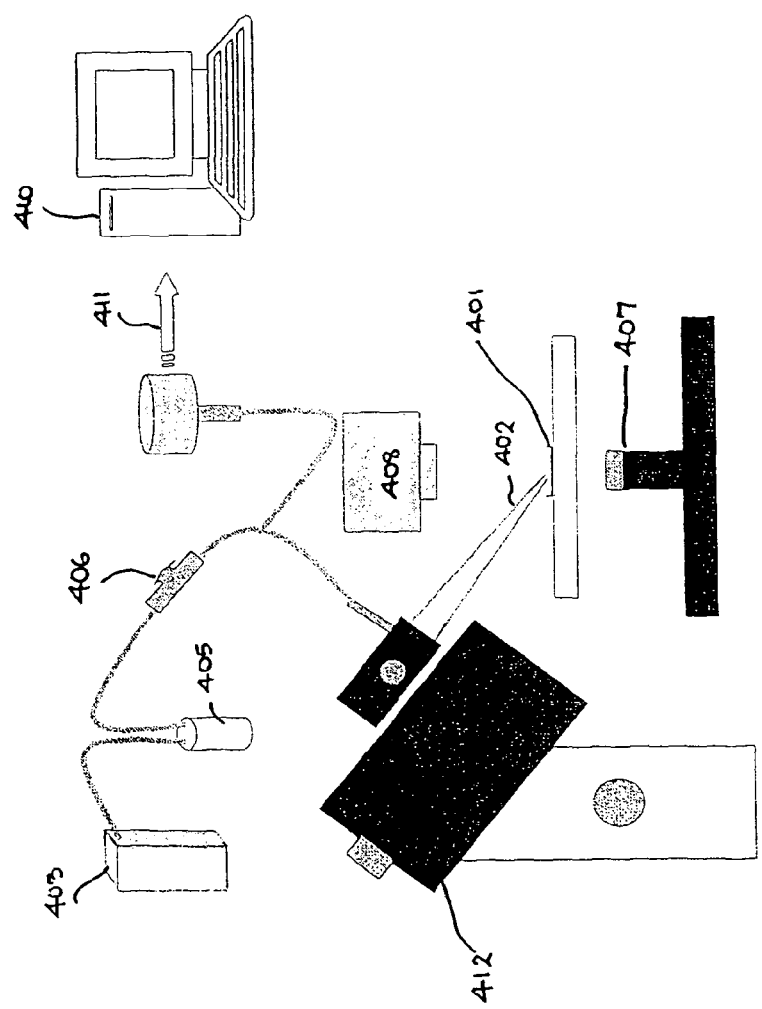
FIG. 4 is a schematic illustration of a cell adhesion measuring apparatus for measuring the adhesion of cells singly.

FIG. 4 is a schematic illustration of the single-cell adhesion measurement apparatus (SCAMA) first described in the paper by Palmer et al. (2008).

Human breast cancer cells from the MDA-MB-231 cell line were plated at a density of $2.5 \times 10^4$ cells/ml and left to settle in a cell culture dish 401 for 48 hours prior to measurements. Medium was removed and 2 ml of the drug under study was applied for 10 minutes. Adhesion was measured using a glass micropipette 402 connected to a vacuum pump 403 via plastic tubing 404. The tip of the micropipette was drawn to about 20 μm (range, 17-24 μm) tip diameter. The vacuum pump was used to create negative pressure inside a reservoir 405 so that the negative pressure could be applied to the tip of the micropipette by pressing the thumb to the open end of a sealable T-piece 406. The cells were observed using a 20× microscope objective 407 under the illumination of a lamp 408. The pressure was measured using a digital manometer 409 connected to a computer 410 via a RS232 cable 411.

Using a micromanipulator 412, the micropipette 402 was positioned on the periphery of a single cell. Upon closing of the T-piece 406, the negative pressure was applied to the cell under investigation and, at the exact moment that the cell was observed to be detached from the culture dish 401, the pressure was released by opening the T-piece 406. The negative pressure required to detach the cell was recorded on the computer as a pressure spike. The peak of the spike ("detachment negative pressure" (DNP)) was used as a measure of the cell's adhesiveness. Using this technique, several recordings could be made from a single dish within minutes.

To simulate hypoxic conditions for the cells, hypoxia was chemically induced by application of hydrogen peroxide (1-500 μM) for the final 24 hours before testing.

In order to test for the reversibility of a given effect, the pharmacological agent was washed off, fresh medium was added and the plate was incubated for a further 10 minutes prior to re-measurement. Each treatment was carried out on at least two dishes of cells, at least 100 cells per dish were measured, and the experiment was repeated three times (with corresponding controls).

Lateral Motility Assay

This assay was used to represent the "free" motility of cancer cells during local spreading. FIG. 5(a) is a plan view from above of a cell culture dish 501 having a semi-confluent layer of cells 502 on its surface, the cells being in an aqueous medium 503.

In order to determine lateral motility, a "wound-heal ("scratch")" test was carried out, in which a scratch 504 of ~0.5 mm was made through the layer of cells, as shown in FIG. 5(b) which is a side sectional view of the cell culture dish.

During the period of 24 hours following the formation of the scratch, the cells moved into the gap.

FIGS. 5(c) and 5(d) are schematic plan views of the cell culture dish 501 at time t=zero when the width of the scratch 504 is $w_0$ and time t=24 hours when the width of the scratch 504 is $w_{24}$, respectively.

Transverse Migration Assay

This assay was used to represent the ability of cells to migrate as they intra/extravasate. FIG. 6 shows a schematic side sectional view of a migration chamber 601 having a Transwell® insert 602 separating the chamber into two sections which, for convenience, will be referred to as the upper 603 and lower 604 sections of the chamber. The insert 602 has a migration filter membrane 605 in its base with 8 μm pores 606 extending therethrough.

Cells 607 were plated at a density of $2 \times 10^4$/ml on the filter membrane 605 and placed under a growth medium 608 containing 1% foetal bovine serum (FBS). A chemotactic gradient was created across the filter membrane 605 by placing growth medium 609 containing 10% FBS in the lower section 604 of the chamber.

Cells were allowed to migrate across the filter membrane 605 over a period of 24 hours, cells migrating and adhering to the underside of the filter membrane 605.

At the end of each assay, non-migrated cells were removed from the upper surface of the insert 602 with two different swabs The number of cells migrating to the underside of the insert 602 was determined using crystal violet staining. Migrated cells were fixed for 15 minutes with ice-cold methanol. Then 0.5% crystal violet (in 25% methanol) was added for 15 minutes. The inserts were swabbed again and then washed in water and allowed to dry. Cells were then counted using twelve separate fields of view per insert (×200 magnification).

Invasion Assay

This assay is an extension of the transverse migration assay described above. To "invade", the cells need both (i) to move as in the transverse migration assay and (ii) secrete a proteolytic enzyme to digest their surroundings. The ability of cells to invade neighbouring tissues by enzyme secretion was therefore assessed by using a layer of Matrigel™ (BD Biosciences) spread across the porous membrane of a Transwen insert. Matrigel™ is composed of laminin, collagen IV, nidogcn/enactin and proteoglycan—a composition comparable to basement membrane proteins.

FIG. 7 is a schematic side sectional view of an invasion chamber 701 having a Transwell® insert 702 separating the chamber into upper 703 and lower 704 sections. The insert 702 has a migration filter membrane 705 in its base with 8 μm pores 706 extending therethrough. A layer 707 of Matrigel™ is shown coating the filter membrane 705.

Cells 708 were plated at a density of $2×10^4$ /ml onto the Matrigel™ layer 707 in 24-well plates (Becton-Dickinson) according to the manufacturers' instructions. 50 µl Matrigel™ was seeded at a 1:7 dilution (10 mg/ml stock) onto the inserts and left overnight. Prior to seeding with the cells the Matrigel™ was rehydrated using medium with no additions. This medium was removed prior to seeding the cells.

Cells were plated in a 1-5 FBS chemotactic gradient overnight (12 hours). The nutrient concentration in the medium 709 in the upper section 703 of the chamber was less than the concentration of nutrient in the medium 710 in the lower section 704 to induced movement of the cells through the Matrigel™ layer 707 and through the pores 706 to the underside of the filter membrane 705. At the end of each assay, non-invaded/non-migrated cells were removed from the upper surface of the insert 702 with two different swabs.

The number of cells invading to the underside of the insert 702 was determined using crystal violet staining. Invaded cells were fixed for 15 minutes with ice-cold methanol. Then 0.5% crystal violet (in 25% methanol) was added for 15 minutes. The inserts were swabbed again and then washed in water and allowed to dry. Cells were then counted using twelve separate fields of view per insert (×200 magnification). If the difference in the average number of cells invading the two control inserts was more than 40%, the experiment was rejected.

Cell Viability Assay

Cells were seeded at a density of $5×10^4$ cells/ml in 35 mm Falcon tissue culture dishes. After treatment with a given drug, the medium was removed and replaced with 800 µl of growth medium and 200 µl 0.4% trypan blue (Sigma, Dorset, UK) and incubated for 10 minutes in the incubator. The trypan blue was removed and the cells were washed once with 3 ml growth medium. For each treatment, cells from 30 random fields of view were counted under 100× magnification. The number of dead cells, stained blue, was counted in each field of view. The data were expressed as percentages of living cells out of the total number of cells in given fields of view. The percentages were averaged and differences between control and treatment were compared from at least three independent experiments.

Cell Growth (Proliferation) Assay

Cells were plated at $2×10^4$ cells/ml in 24-well plates (Becton-Dickinson) and allowed to settle overnight. The cells were then treated for the required time of incubation (24 hours +), with medium changes every 24 hours. At the end of the treatment, the medium was removed, and this was followed by the colorimetric 3-[4,5-dimethylthiazol-2-yl]-2,5-diphenyltetrazolium bromide (MTT) assay (Grimes et al., 1995). Briefly, 0.1 ml MTT (5 mg/ml made up in the growth medium) and 0.4 ml growth medium was added in each well and the plate was incubated for 3-4 hours at 37° C. The medium was then removed from the chambers and replaced with 0.5 ml dimethyl sulfoxide (DMSO) and 0.063 ml glycine buffer (0.1 M glycine and 0.1 M NaCl; pH 10.5). Absorbance at 570 nm was determined 15 minutes after the addition of the glycine buffer. Results were calculated as means of nine repeats of each of the treatment vs. control spectrophotometer readings from individual invasion wells.

Tissue Culture

Experiments were carried out on two strongly metastatic cell lines:
(i) human metastatic breast cancer MDA-MB-231, and
(ii) rat strongly metastatic prostate cancer Mat-LyLu.

Cells were cultured using known methods (e.g. Grimes et al., 1995; Fraser et al., 2005).

Normoxic and Hypoxic Conditions

With the exception of single cell adhesion tests, which are discussed in the following paragraph, experiments were carried out under either;
(i) normal normoxic conditions (95% oxygen, 5% carbon dioxide), or
(ii) following 24 hours hypoxic pre-treatment (2% $O_2$, 5% $CO_2$, 93% $N_2$) continued during the assays.

In the single cell adhesion experiments, hypoxia was induced chemically by application of hydrogen peroxide (1-500 µM) for 24 hours.

EXAMPLES

Example 1

Effects of Chemical Hypoxia on the Single-Cell adhesion of MDA-MB-231 Cells

Chemical hypoxia was induced by treating cells with different concentrations of hydrogen peroxide for 24 hours. Single-cell adhesion was measured using the technique described above and illustrated in FIG. 4. The change in detachment negative pressure (ΔDNP) was expressed as a percentage versus a control population of untreated cells. Hypoxia reduced the cell adhesion and increasing the concentration of hydrogen peroxide, i.e., increasing the degree of hypoxia, led to greater reduction in cell adhesion as shown in FIG. 8. In this figure, the vertical axis represents the change in detachment negative pressure (ΔDNP), increasing downwardly so that a higher negative value is indicative of a cell's lower adhesion and, hence, its tendency to detachment. The horizontal axis is a logarithmic scale of hydrogen peroxide concentration, increasing from left to right.

Human breast cancer cells from the MDA-MB-231 cell line were plated in a cell culture dish at a density of $2.5×10^4$ cells/ml and left to settle for 48 hours prior to measurements. The cells were subjected to hydrogen peroxide concentrations of 1 µM, 10 µM and 100 µM and the negative pressure required to detach cells from the bottom of the cell culture dish was measured. At each concentration of hydrogen peroxide, measurements were taken on at least two dishes of cells for at least 100 cells per dish. The experiment was repeated three times and the measurements of detachment negative pressure are presented in FIG. 8 as means±SEM.

In FIG. 8, the data point 801 shows that cells exposed to hydrogen peroxide at a concentration of 1 µM had a mean detachment negative pressure of approximately −9%, data point 802 shows that cells exposed to hydrogen peroxide at a concentration of 10 µM had a mean detachment negative pressure of approximately −14%, and data point 803 shows that cells exposed to hydrogen peroxide at a concentration of 100 µM had a mean detachment negative pressure of approximately −20%. Hence, increasing the concentration of hydrogen peroxide decreased the adhesion of the cells and made them easier to detach. In other words, increasing the severity of the hypoxic conditions led to an increase in the detachability of the cells.

Example 2

Effects of Ranolazine on the Single-Cell Adhesion of MDA-MB-231 Cells Under Normoxic and Hypoxic Conditions Single-cell adhesion was measured using the technique described above and illustrated in FIG. 4 for human MDA- MB-231 cells exposed to different concentrations of ranolazine and under normoxic and hypoxic conditions. Ranolazine increased the substrate adhesion of cells under normoxia in a dose dependent manner. The dose-dependent increase in the adhesion of cells was even more marked under hypoxia—See FIG. 9. In this figure, the vertical axis represents a measure of the adhesion of cells. The horizontal axis is a logarithmic scale of ranolazine concentration, increasing from left to right. Data were collected from n=7 independent experiments for each condition and are presented in FIG. 9 as means±SEM.

Human breast cancer cells from the MDA-MB-231 cell line were plated in cell culture dishes at a density of 2.5×10$^4$ cells/ml and left to settle for 48 hours prior to measurements.

In the normoxia experiments (curve 901), different dishes of the plated cells were treated with ranolazine at concentrations of 0.1 µM, 0.5 µM, 1 µM, 10 µM, 20 µM and 100 µM. At the lowest concentration of 0.1 µM, ranolazine had no effect on the adhesion of the cells. At concentrations of 0.5 µM, 1 µM, 10 µM, 20 µM and 100 µM of Ranolazine, the adhesion increased in a dose dependent mariner; the amount of increase in adhesion appeared to level off at a concentration of 100 µM Ranolazine.

In the hypoxia experiments (curve 902), hypoxia was chemically induced by treating the cells with hydrogen peroxide (50 µmol) for 24 hours. Different dishes of the plated cells were treated with ranolazine at concentrations of 0.1 µM µM, 10 µM and 100 µM Even at the lowest concentration of 0.1 µM ranolazine the adhesion of the hypoxic cells and the adhesion increased and continued to increase in a dose dependent manner for concentrations of Ranolazine of 1 µM 10 µM and 100 µM The amount of increase in adhesion appeared to level off at a concentration of 100 µM. Ranolazine and the curves for nonnoxic and hypoxic experiments appeared to converge at around this concentration.

From a comparison of the effects of ranolazine on adhesion of cells under normoxia (curve 901) and hypoxia (curve 902), the effect of ranolazine was approximately 10-fold greater in hypoxia before convergence at the higher drug concentrations.

Example 3

Effects of Ranolazine on the Lateral Motility of MDA-MB-231 Cells Under Normoxia and Hypoxia Lateral motility of the cells was measured using the technique described above and illustrated in FIG. 5.

Referring to FIG. 10, the vertical axis represents the motility index of the measured cells, with a reference point for normal motility being represented by the control sample (block 1001 of the histogram) of MDA-MB-231 cells under normoxia and without drug, normalised to 100%. Across the horizontal axis, the set of results for experiments conducted under normoxia is plotted on the left-hand side and the set of results for experiments conducted under hypoxia is plotted on the right-hand side. For each set of results, the concentration of ranolazine used increases from left to right.

Block 1005 is the result obtained for the control sample (without drug) for MDA-MB-231 cells under conditions of hypoxia. From a comparison of blocks 1001 and 1005 it can be seen that hypoxia increased motility.

Human breast cancer cells from the MDA-MB-231 cell line were treated with different concentrations of ranolazine under normoxia, and hypoxia. In the normoxia experiments, the motility of the cells was measured after treating them with no drug (control) and ranolazine at concentrations of 1 µM, 10 µM and 100 µM. The results are shown in FIG. 10 as blocks 1001, 1002, 1003 and 1004, respectively. Increasing the concentration of ranolazine reduced the lateral motility of the cells, but only the reduction at a concentration of 100 µM ranolazine was statistically significant.

Similarly, in the hypoxia experiments, the motility of the cells was measured after treating them with no drug (control) and ranolazine at concentrations of 1 µM, 10 µM and 100 µM. The results are shown in FIG. 10 as blocks 1005, 1006, 1007 and 1008, respectively. Increasing the concentration of ranolazine reduced the lateral motility of the cells and each concentration of ranolazine tested gave a statistically significant reduction in lateral motility of the cells.

Data were collected from n=3 independent experiments for each condition and are presented as means±SEM. (*) indicates significance at $P<0.05$; (**) indicates significance at $P<0.01$.

Example 4

Effects of Ranolazine on the Transverse Migration of MDA-MB-231 Cells Under Normoxia and Hypoxia Transverse migration of the cells was measured using the technique described above and illustrated in FIG. 6.

Referring to FIG. 11, the vertical axis represents relative values for transverse migration of the measured cells, with a reference point for normal transverse migration being represented by the control sample (block 1101) of MDA-MB-231 cells under normoxia and without drug, normalised to 100%. Across the horizontal axis, the set of results for experiments conducted under normoxia is plotted on the left-hand side and the set of results for experiments conducted under hypoxia is plotted on the right-hand side. For each set of results, the concentration of ranolazine used increases from left to right.

Block 1105 is the result obtained for the control sample (without drug) for MDA-MB-231 cells under conditions of hypoxia. From a comparison of blocks 1101 and 1105 it can be seen that hypoxia increased transverse migration.

Human breast cancer cells from the MDA-MB-231 cell line were treated with different concentrations of ranolazine under normoxia, and hypoxia. In the normoxia experiments, the migration of the cells was measured after treating them with no drug (control) and ranolazine at concentrations of 1 µM, 10 µM and 100 µM. The results are shown in FIG. 11 as blocks 1101, 1102, 1103 and 1104, respectively. Increasing the concentration of ranolazine reduced the transverse migration of the cells only slightly and the results were not statistically significant.

In the hypoxia experiments, the migration of the cells was measured after treating them with no drug (control) and ranolazine at concentrations of 1 µM, 10 µM and 100 µM. The results are shown in FIG. 10 as blocks 1105, 1106, 1107 and 1108, respectively. Ranolazine at concentrations of 1 µM and 10 µM reduced the transverse migration of the cells in a statistically significant way; ranolazine at a concentration of 100 µM also reduced the transverse migration of the cells, but the reduction was not statistically significant.

Data were obtaining from n=3 independent experiments for each condition and are presented as means±SEM. (*) indicates significance at $P<0.05$.

Example 5

Effects of Ranolazine on the Invasiveness of MDA-MB-231 Cells Under Normoxia and Hypoxia (No Pre-Treatment)

The invasiveness of the cells was measured using the technique described above and illustrated in FIG. 7.

Referring to FIG. 12, the vertical axis represents relative values for invasiveness of the measured cells, with a reference point for normal invasiveness being represented by the control sample (block 1201) of MDA-MB-231 cells under normoxia and without drug, normalised to 100%. Across the horizontal axis, the set of results for experiments conducted under normoxia is plotted on the left-hand side and the set of results for experiments conducted under hypoxia is plotted on the right-hand side. For each set of results, the concentration of ranolazine used increases from left to right.

FIG. 12 also includes results for an additional pair of controls, labelled in the drawing as blocks 1202 and 1208. In these additional controls, cells were exposed to the toxin tetrodotoxin (TTX) whose binding site is located at the pore opening of the VGSC. The TTX measurement is a positive control confirming that sodium channel activity is indeed contributing (potentiating) the metastatic cell behaviour under investigation. It should be noted that, at the concentrations of TTX used here (10 μmol), blocking of the VGSC is not total. Hence, particularly at the higher concentrations tested, the drug (ranolazine) appears to be more potent than the toxin (TTX).

Block 1207 is the result obtained for the control sample (without drug) for MDA-MB-231 cells under conditions of hypoxia. From a comparison of blocks 1201 and 1207 it can be seen that hypoxia increased invasiveness.

Human breast cancer cells from the MDA-MB-231 cell line were treated with different concentrations of ranolazine under normoxia, and hypoxia. In the normoxia experiments, the invasiveness of the cells was measured after treating them with no drug (control) and ranolazine at concentrations of 10 μM, 20 μM, 50 μM and 300 μM. The results are shown in FIG. 12 as blocks 1201, 1203, 1204, 1205 and 1206, respectively. Treatment with ranolazine reduced the migration of the cells at concentrations of 10 μM, 20 μM and 300 μM, but the effect of ranolazine at a concentration of 50 μM was not statistically significant.

In the hypoxia experiments, the migration of the cells was measured after treating them with no drug (control) and ranolazine at concentrations of 5 μM, 10 μM, 20 μM, 50 μM and 300 μM. The results are shown in FIG. 12 as blocks 1207, 1209, 1210, 1211, 1212 and 1213, respectively. Treatment with ranolazine reduced the migration of the cells at concentrations of 20 μM, 50 μM and 300 μM, but the effect of ranolazine at concentrations of 5 μM and 10 μM was not statistically significant.

Data were collected from n=3 independent experiments for each condition and are presented as means±SEM. (*) indicates significance at P<0.05; (**) indicates significance at P<0.01.

Example 6

Effects of Ranolazine on the Invasiveness of MDA-MB-231 Cells Under Normoxia and Hypoxia with Pre-Treatment of the Cells As the reduction in invasiveness at low concentrations of ranolazine under hypoxia was not statistically significant, a modified version of the invasiveness assay was carried out in which the cells were pre-treated with ranolazine for different periods in comparison to corresponding control conditions (i.e., no ranolazine applied).

FIG. 13(a) and (b) show the effect of 5 μM ranolazine (ran) on invasion of MDA-MB-231 cells under conditions of hypoxia in vitro. The histograms indicate the number of MDA-MB-231 cells invading following treatment with 5 μM ranolazine for different periods in comparison to corresponding control conditions (i.e. no ranolazine applied).

In FIG. 13(a), block 1301 represents the invasiveness result obtained under control conditions (no drug) for cells invading over the 24 hour duration of the assay (i.e., effectively no pre-treatment was used). Block 1302 represents the invasiveness result for cells treated with 5 μM ranolazine and invading over the 24 hour duration of the assay (no pre-treatment). The effect on invasiveness of cells treated with 5 μM ranolazine was not statistically significant.

In FIG. 13(b), block 1303 represents the invasiveness result obtained under control conditions (no drug) for cells invading over the 24 hour duration of the assay (i.e., effectively no pre-treatment was used). Block 1304 represents the invasiveness result for cells pre-treated with 5 μM ranolazine for 72 hours and invading over the 24 hour duration of the assay. There was a very significant reduction in the invasiveness of cells pre-treated with 5 μM ranolazine for 72 hours.

In each of FIGS. 13(a) and (b), the number of "cells invading" denotes the average of cell number counted in 24 randomly chosen fields of view from two separate inserts (experiments).

FIG. 13(c) to (e) show the effect of 25 μM ranolazine (ran) on invasion of MDA-MB-231 cells under conditions of hypoxia in vitro. The histograms indicate the number of MDA-MB-231 cells invading following treatment with 25 μM ranolazine for different periods in comparison to corresponding control conditions (i.e. no ranolazine applied).

In FIG. 13(c), block 1305 represents the invasiveness result obtained under control conditions (no drug) for cells invading over the 24 hour duration of the assay (i.e., effectively no pre-treatment was used). Block 1306 represents the invasiveness result for cells treated with 25 μM ranolazine and invading over the 24 hour duration of the assay (no pre-treatment). Cells treated with 5 μM ranolazine were less invasive than untreated cells in a statistically significant way.

In FIG. 13(d), block 1307 represents the invasiveness result obtained under control conditions for cells maintained for 24 hours without drug and invading over the following 24 hours prior to measurement. Block 1308 represents the invasiveness result for cells pre-treated for 24 hours with 25 μM ranolazine and invading over the following 24 hours prior to measurement. Cells pre-treated with 25 μM ranolazine for 24 hours before commencing the 24 hour long assay were significantly less invasive than untreated cells.

In FIG. 13(e), block 1309 represents the invasiveness result obtained under control conditions for cells maintained for 48 hours without drug and invading over the following 24 hours prior to measurement. Block 1310 represents the invasiveness result for cells pre-treated for 48 hours with 25 μM ranolazine and invading over the following 24 hours prior to measurement. Cells pre-treated with 25 μM ranolazine for 48 hours before commencing the 24 hour long assay were again significantly less invasive than untreated cells.

As above, the number of "cells invading" in the histograms of FIGS. 13(c) to (e) denotes the average of cell number counted in 24 randomly chosen fields of view from two separate experiments.

At both the concentrations tested (5 µM and 25 µmol, pre-treatment of the cells with ranolazine led to a statistically significant reduction in their invasiveness. Such pre-treatment of the cells with the drug in an in vitro test is considered to be representative of in vivo treatment, where the patient receives a continual therapeutic dose of the drug.

Example 7

Effects of Ranolazine on the Growth of MDA-MB-231 Cells Under Normoxia and Hypoxia The growth of the cells was measured using the technique described above under the heading "Cell growth (proliferation) assay".

Referring to FIG. 14, the vertical axis represents the total cell number in a plated sample, with reference points for normal growth being represented by the control samples (blocks 1401, 1405 and 1409) of MDA-MB-231 cells under normoxia and without drug at commencement, after 24 hours and after 48 hours, respectively. Across the horizontal axis, three sets of results are shown for measurements taken at commencement, after 24 hours and after 48 hours of growth. Here, the term "growth" includes cell proliferation and cell death and in this assay, both with and without drug, there was an overall increase in the number of cells over time. For each of the three sets of results, the concentration of ranolazine used increases from left to right.

Human breast cancer cells from the MDA-MB-231 cell line were treated with different concentrations of ranolazine under normoxia.

At commencement (0 hours), the number of cells was measured after treating them with no drug (control) and ranolazine at concentrations of 1 µM, 10 µM and 100 µM. The results are shown in FIG. 14 as blocks 1401, 1402, 1403 at 1404, respectively. Increasing the concentration of ranolazine had no effect upon the cell number at commencement.

After 24 hours, the number of cells at each concentration of ranolazine was counted again. The results are shown in FIG. 14 as blocks 1405, 1406, 1407 and 1408. There was no significant difference between the number of cells in control sample (block 1405) and the numbers of cells in the samples treated with ranolazine at concentrations of 1 µM, 10 µM and 100 µM (blocks 1406, 1407 and 1408, respectively).

After a further 24 hours (48 hours in total), the number of cells at each concentration of ranolazine was counted again. The results are shown in FIG. 14 as blocks 1409, 1410, 1411 and 4012. There was no statistically significant difference between the number of cells in control sample (block 1409) and the numbers of cells in the samples treated with ranolazine at concentrations of 1 µM, 10 µM and 100 µM (blocks 1410, 1411 and 4012, respectively).

Similarly, in the hypoxia experiments, the motility of the cells was measured after treating them with no drug (control) and ranolazine at concentrations of 1 µM, 10 µM and 100 µM. The results are shown in FIG. 10 as blocks 1005, 1006, 1007 and 1008, respectively. Increasing the concentration of ranolazine reduced the lateral motility of the cells, with the result that each concentration of ranolazine being statistically significant.

Data were collected from n=3 independent experiments for each condition and are presented as means±SEM.

The same concentrations of ranolazine under hypoxia also did not affect the growth of the MDA-MB-231 cells (results not shown in FIG. 14).

Example 8

Effects of Ranolazine on the Viability of MDA-MB-231 Cells Under Normoxia

The viability of the cells was measured using the technique described above under the heading "Cell viability assay".

Referring to FIG. 15, the vertical axis represents the relative viability of cells in a plated sample, with a reference point for normal viability being represented by the control sample (block 1501) of MDA-MB-231 cells under normoxia and without drug. The concentration of ranolazine with which different samples of the cells were treated is plotted across the horizontal axis, increasing from left to right.

Human breast cancer cells from the MDA-MB-231 cell line were treated with different concentrations of ranolazine under normoxia. The viability of the cells was measured after treating them for 48 hours with no drug (control) and ranolazine at concentrations of 1 µM, 10 µM and 100 µM. the results are shown in FIG. 15 as blocks 1501, 1502, 1503 and 1504, respectively. There was no effect of ranolazine on cell viability.

Data were collected from n=3 independent experiments for each condition and are presented as means±SEM.

Example 9

Effects of Ranolazine on Transverse Migration of Mat-LyLu Cells Under Normoxia and Hypoxia Transverse migration of the cells was measured using the technique described above and illustrated in FIG. 6.

Referring to FIG. 16, the vertical axis represents relative values for transverse migration of the measured cells, with a reference point for normal transverse migration being represented by the control sample (block 1601) of Mat-LyLu cells under normoxia and without drug, normalised to 100%. Across the horizontal axis, the set of results for experiments conducted under normoxia is plotted on the left-hand side and the set of results for experiments conducted under hypoxia is plotted on the right-hand side. For each set of results, the concentration of ranolazine used increases from left to right.

FIG. 16 also includes results for an additional pair of controls, labelled in the drawing as blocks 1602 and 1607. In these additional controls, cells were exposed to the toxin tetrodotoxin (TTX) whose binding site is located at the pore opening of the VGSC. The TTX measurement is a positive control confirming that sodium channel activity is indeed contributing to (potentiating) the metastatic cell behaviour under investigation. It should be noted that, at the concentrations of TTX used here (1 µmol), blocking of the VGSC is not total. Hence, particularly at the higher concentrations tested, the drug (ranolazine) appears to be more potent than the toxin (TTX).

Block 1606 is the result obtained for the control sample (without drug) for Mat-LyLu cells under conditions of hypoxia. From a comparison of blocks 1601 and 1606 it can be seen that hypoxia increased transverse migration.

Rat prostate cancer cells from the Mat-LyLu cell line were treated with different concentrations of ranolazine under normoxia, and hypoxia. In the normoxia experiments, the migration of the cells was measured after treating them with no drug (control) and ranolazine at concentrations of 20 µM, 50 µM and 300 µM. The results are shown in FIG. 16 as blocks 1601, 1603, 1604 and 1605, respectively. Increasing the concentration of ranolazine reduced the transverse migration of the cells at concentrations of ranolazine of 20 µM and 50 µM. The effect of ranolazine on transverse migration at a concentration of 300 µM was not statistically significant.

In the hypoxia experiments, the migration of the cells was measured after treating them with no drug (control) and ranolazine at concentrations of 20 µM, 50 µM and 300 µM. The results are shown in FIG. 16 as blocks 1606, 1608, 1609 and 1610, respectively. Ranolazine at concentrations of 20 µM, 50 µM and 300 µM each reduced the transverse migration of the cells in a statistically significant way.

Data were obtained from n≥3 independent experiments for each condition and are presented as means±SEM. (*) indicates significance at $P<0.05$ compared to control.

Example 10

Effects of Ranolazine on Invasiveness of Mat-LyLu Cells Under Normoxia and Hypoxia The invasiveness of the cells was measured using the technique described above and illustrated in FIG. 7.

Referring to FIG. 17, the vertical axis represents relative values for invasiveness of the measured cells, with a reference point for normal invasiveness being represented by the control sample (block 1701) of Mat-LyLu cells under normoxia and without drug, normalised to 100%. Across the horizontal axis, the set of results for experiments conducted under normoxia is plotted on the left-hand side and the set of results for experiments conducted under hypoxia is plotted on the right-hand side. For each set of results, the concentration of ranolazine used increases from left to right.

FIG. 17 also includes results for an additional pair of controls, labelled in the drawing as blocks 1702 and 1707. In these additional controls, cells were exposed to the toxin tetrodotoxin (TTX) whose binding site is located at the pore opening of the VGSC. The TTX measurement is a positive control confirming that sodium channel activity is indeed contributing (potentiating) the metastatic cell behaviour under investigation. It should be noted that, at the concentrations of TTX used here (1 µM), blocking of the VGSC is not total. Hence, particularly at the higher concentrations tested, the drug (ranolazine) appears to be more potent than the toxin (TTX).

Block 1706 is the result obtained for the control sample (without drug) for Mat-LyLu cells under conditions of hypoxia. From a comparison of blocks 1701 and 1706, it does not appear that hypoxia affected the invasiveness of the cells. I Rat prostate cancer cells from the Mat-LyLu cell line were treated with different concentrations of ranolazine under normoxia, and hypoxia. In the normoxia experiments, the invasiveness of the cells was measured after treating them with no drug (control) and ranolazine at concentrations of 20 µM, 50 µM and 300 µM. The results are shown in FIG. 17 as blocks 1701, 1703, 1704 and 1705, respectively. Treatment with ranolazine reduced the migration of the cells in a statistically significant way at each of the tested concentrations of ranolazine.

In the hypoxia experiments, the migration of the cells was measured after treating them with no drug (control) and ranolazine at concentrations of 20 µM, 50 µM and 300 µM. The results are shown in FIG. 17 as blocks 1706, 1708, 17091710, respectively. Treatment with ranolazine reduced the migration of the cells in a statistically significant way at each of the tested concentrations of ranolazine.

Data were obtained from n>3 independent experiments for each condition and are presented as means±SEM. (*) indicates significance at $P<0.05$ compared to normoxia control; (*) indicates significance at $P<0.05$ compared to both normoxia and hypoxia control.

Example 11

Effects of Ranolazine on Growth of Mat-LyLu Cells

The growth of the cells was measured using the technique described above under the heading "Cell growth (proliferation) assay".

Referring to FIG. 18, the vertical axis represents the total cell number in a plated sample, with a reference point for normal growth being represented by the control sample (blocks 1801) of Mat-LyLu cells under normoxia and without drug normalised to 100%. Across the horizontal axis, the set of results for experiments conducted under normoxia is plotted on the left-hand side and the search of results for experiments conducted under hypoxia is plotted on the right-hand side. For each set of results, the concentration of ranolazine used increases from left to right. Note that the term "growth" includes cell proliferation and cell death.

Rack prostate cancer cells from the Mat-LyLu cell line were treated with different concentrations of ranolazine under normoxia, and hypoxia. In the normoxia experiments, the number of cells was measured after treating them for 24 hours with no drug (control) and ranolazine at concentrations of 20 µM, 50 µM and 300 µM. The results are shown in FIG. 18 as blocks 1801, 1802, 1803 and 1804, respectively. Increasing the concentration of ranolazine did not result in any statistically significant effect on the number of cells.

Similarly, in the hypoxia experiments, the number of cells was measured after treating them for 24 hours with no drug (control) and ranolazine at concentrations of 20 µM, 50 µM and 300 µM. The results are shown in FIG. 18 as blocks 1805, 1806, 1807 and 1808, respectively. Increasing the concentration of ranolazine did not result in any statistically significant effect on the number of cells at concentrations of ranolazine of 20 µM and 50 µM. At a concentration of ranolazine of 300 µM, there was a reduction in the number of cells.

In summary, growth of Mat-LyLu cells was unchanged in all conditions tested except with 300 µM ranolazine under hypoxia Data were collected from n=3 independent experiments for each condition and are presented as means±SEM. (*) indicates significance at $P<0.05$ compared to both normoxia and hypoxia control, while (x) indicates no statistical difference.

Example 12

Effects of Ranolazine on Viability of Mat-LyLu Cells

Cells were treated with different concentrations of ranolazine at [20 µM], [50 µM] and [300 µM] for 24 hours under normoxic or hypoxic (2% O2) conditions. The results obtained are shown in FIG. 19. There was no effect of ranolazine on cell viability regardless of concentration and regardless of whether the cells were under normoxic or hypoxic conditions. Data were collected from n=3 independent experiments for each condition and are presented as means±SEM.

Example 13

Effects of Riluzole on the Lateral Motility of MDA-MB-231 Cells Under Normoxia and Hypoxia Lateral motility of the cells was measured using the technique described above and illustrated in FIG. 5. Referring to FIG. 20, block 2001 of the histogram shows the motility index for the control sample of MDA-MB-231 cells under normoxia and without drug, normalised to 100%. Block 2005 is the corresponding control sample (without drug) for MDA-MB-231 cells under conditions of hypoxia. From a comparison of blocks 2001 and 2005 it can be seen that hypoxia increased motility significantly.

Cells were treated with different concentrations of riluzole ([1 µM], [10 µM], and [100 µM]) under normoxia, and hypoxia. Increasing the concentration of riluzole reduced the lateral motility of the cells; the effect was greater under hypoxia. Data were collected from n=5 independent experiments for each condition and are presented as means±SEM. (*) indicates significance at P<0.05; (**) indicates significance at P<0.01.

Example 14

Effects of Riluzole on the Transverse Migration of MDA-MB-231 Cells Under Normoxia and Hypoxia Transverse migration of the cells was measured using the technique described above and illustrated in FIG. 6. Referring to FIG. 21, block 2101 represents the proportion of transverse migration observed for the control sample of MDA-MB-231 cells under normoxia and without drug, normalised to 100%. Block 2105 is the corresponding control sample (without drug) for MDA-MB-231 cells under conditions of hypoxia. From a comparison of blocks 2101 and 2105, it appeared that hypoxia increased transverse migration but the increase was not statistically significant for the number of test runs completed.

Cells were treated with different concentrations of riluzole ([1 µM], [10 µM], and [100 µM]) under normoxia, and hypoxia. Under normoxia, treatment with riluzole reduced the transverse migration of the cells in a statistically significant way at concentrations of 1 µM and 100 µM. Under hypoxia, increasing the concentration of riluzole reduced the transverse migration in a statistically significant way. Data were obtaining from n=3 independent experiments for each condition and are presented as means±SEM. (*) indicates significance at P<0.05.

Example 15

Effects of Riluzole on the Invasiveness of MDA-MB-231 Cells Under Normoxia and Hypoxia (No Pre-Treatment)

The invasiveness of the cells was measured using the technique described above and illustrated in FIG. 7. Results are shown in FIG. 22. Riluzole at a concentration of 5 µNA significantly inhibited invasiveness even without pre-treatment. The number of "cells invading" denotes the average of cell number counted in 24 randomly chosen fields of view from two separate inserts (experiments).

Example 16

Effects of Riluzole on the Invasiveness of MDA-MB-231 Cells Under Normoxia and Hypoxia (72 Hours Pre-Treatment)

The invasiveness of the cells was measured using the same technique as described above for Example 6 with the cells being pre-treated for 72 hours with riluzole at a concentration of 5 µM. Results are shown in FIG. 23. Cells pre-treated with riluzole for 72 hours at a concentration of 5 µM also showed significantly inhibited invasiveness. As above, the number of "cells invading" denotes the average of cell number counted in 24 randomly chosen fields of view from two separate inserts.

Example 18

Effects of Riluzole on the Growth of MDA-MB-231 Cells Under Normoxia and Hypoxia Cells were treated with different concentrations of riluzole at [1 µM], [10 µM] and [100 µM] for 48 hours. The results obtained are shown in FIG. 24. Riluzole at a concentration of 100 µM reduced the proliferation of the cells in a statistically significant way at 24 hours and after 48 hours. Data were collected from n=3 independent experiments for each condition and are presented as means±SEM. (*) indicates significant level at P<0.05.

Example 19

Effects of riluzole on the Viability of MDA-MB-231 Cells Under Normoxia and Hypoxia Cells were treated with different concentrations of riluzole at [1 µM], [10 µM] and [100 µM] for 48 hours. The results obtained are shown in FIG. 25. Riluzole at concentrations of 10 µM and 100 µM decreased the cell viability. Data were collected from n=3 independent experiments for each condition and are presented as means±SEM. (*) indicates significant level at P<0.05.

The same concentrations of ranolazine under hypoxia also did not affect the growth of the MDA-MB-231 cells (results not shown in FIG. 25).

Example 20

Effects of Riluzole on Matrigel™ Invasion of Mat-LyLu Cells Under Normoxia and Hypoxia (no Pre-Treatment)

The invasiveness of the cells was measured using the technique described above and illustrated in FIG. 7. Referring to FIG. 26, block 2601 shows the invasion index for the control sample of Mat-LyLu cells under normoxia and without drug, normalised to 100%. Block 2604 is the corresponding control sample (without drug) for Mat-LyLu cells under conditions of hypoxia. From a comparison of blocks 2601 and 2604 it can be seen that hypoxia increased invasion in a statistically significant way.

Riluzole at a concentration of 1 µM significantly inhibited invasiveness under normoxia and hypoxia even without pre-treatment. Data were obtained from n≥3 independent experiments for each condition and are presented as means±SEM. (*) indicates significance at P<0.05 compared to control.

Example 21

Effects of Riluzole on Growth of Mat-LyLu Cells

Cells were treated with different concentrations of riluzole at [3 µM], [5 µM], [10 µM] and [30 µM] for 24 hours under normoxic or hypoxic (2% $O_2$) conditions. The results obtained are shown in FIG. 27. Riluzole decreased cell proliferation dose dependently under both normoxia and hypoxia; the effect was greater under hypoxia. Data were collected from n=3 independent experiments for each condition and are presented as means±SEM. (*) indicates significance at P<0.05 compared to control; (x) indicates no statistical difference.

Example 22

Effects of Riluzole on Viability of Mat-LyLu Cells

Cells were treated with different concentrations of riluzole at [10 µM], [30 µM], and [100 µM] for 24 h under normoxic or hypoxic (2% $O_2$) conditions. The results are shown in FIG. 28. There was no effect of riluzole (10-100 µM) on cell viability. Data were collected from n=3 independent experiments for each condition and are presented as means±SEM.

Although the invention has been described mainly in relation to ranolazine and riluzole, other substances having the effect of reducing the persistent VGSC current without eliminating the transient current may be used, for example valporate, flecainide, lidocaine, mexiletine or F15845. Further, although the invention has been described mainly in relation to breast and prostate cancer, it is applicable to all metastatic cancers which express voltage gated sodium channels.

REFERENCES

Fraser S P, Diss J K J, Chioni A-M, Mycielska M E, Pan H, Yamaci R, Pani F, Siwy Z, Krasowska M, Grzywna Z, Brackenbury W J, Theodorou D, Koyutürk M, Kaya H, Battaloglu E, De Bella M I, Slade M J, Tolhurst R, Palmieri C, Jiang J, Latchman D S, Coombes R C & Djamgoz MBA (2005). Voltage-gated sodium channel expression and potentiation of human breast cancer metastasis. *Clin Cancer Res.* 11: 5381-5389.

Grimes J A, Fraser S P, Stephens G J, Downing JEG, Laniado M E, Foster C S, Abel P D & Djamgoz MBA (1995). Differential expression of voltage-activated $Na^+$ currents in two prostatic tumour cell lines: contribution to invasiveness in vitro. *FEBS Letters* 369: 290-294.

Palmer C P, Mycielska M E, Burcu H, Osman K, Collins T, Beckerman R, Perrett R, Johnson H, Aydar E & Djamgoz MBA (2008). Single cell adhesion measuring apparatus (SCAMA): application to cancer cell lines of different metastatic potential and voltage-gated $Na^+$ channel expression. *Eur Biophys J.* 37: 359-368.

The invention claimed is:

1. A method for inhibiting metastatic and invasive growth of malignant cells in a cancer patient in need thereof, comprising administering an effective and pharmaceutically acceptable amount to the patient of an inhibitor of a voltage gated sodium channel (VGSC), wherein the effective and pharmaceutically acceptable amount is not lethal to the malignant cells, blocks the persistent part of the VGSC current, and does not block the transient part of the VGSC current, wherein the inhibitor of the VGSC is ranolazine.

2. The method according to claim 1, wherein the VGSC is Nav1.5.

3. The method according to claim 2, wherein the VGSC is the neonatal form.

4. The method according to claim 2, wherein the cancer patient suffers from breast cancer.

5. The method according to claim 1, wherein the VGSC is Nav1.7.

6. The method according to claim 5, wherein the cancer patient suffers from prostate cancer.

7. The method of claim 1, wherein the effective and pharmaceutically acceptable amount is such that the malignant cells are subjected to ranolazine in a concentration of 1 µM to 10 µM.

* * * * *

UNITED STATES PATENT AND TRADEMARK OFFICE
CERTIFICATE OF CORRECTION

| | |
|---|---|
| PATENT NO. | : 11,634,398 B2 |
| APPLICATION NO. | : 16/576178 |
| DATED | : April 25, 2023 |
| INVENTOR(S) | : Mustafa Djamgoz |

It is certified that error appears in the above-identified patent and that said Letters Patent is hereby corrected as shown below:

On the Title Page

Item (71) the Applicant name is listed incorrectly; it should appear as follows:
Celex Oncology Innovations Limited, London (GB)

Item (73) the Assignee name is listed incorrectly; it should appear as follows:
Celex Oncology Innovations Limited, London (GB)

Signed and Sealed this
First Day of August, 2023

Katherine Kelly Vidal
*Director of the United States Patent and Trademark Office*